(12) United States Patent
Lohray et al.

(10) Patent No.: US 7,119,198 B2
(45) Date of Patent: Oct. 10, 2006

(54) TRICYCLIC COMPOUNDS AND THEIR USE IN MEDICINE; PROCESS FOR THEIR PREPARATION AND PHARMACEUTICAL COMPOSITIONS CONTAINING THEM

(75) Inventors: Braj Bhushan Lohray, Hyderabad (IN); Vidya Bhushan Lohray, Hyderabad (IN); Ashok Channaveerappa Bajji, Hyderabad (IN); Shivaramayya Kalchar, Hyderabad (IN); Rajagopalan Ramanujam, Hyderabad (IN); Ranjan Chakrabarti, Hyderabad (IN)

(73) Assignees: Dr. Reddy's Research Foundation, Hyderabad (IN); Reddy-Cheminor, Inc., Bridgewater, NJ (US)

( * ) Notice: Subject to any disclaimer, the term of this patent is extended or adjusted under 35 U.S.C. 154(b) by 0 days.

(21) Appl. No.: 11/182,032

(22) Filed: Jul. 14, 2005

(65) Prior Publication Data

US 2006/0148793 A1   Jul. 6, 2006

Related U.S. Application Data

(60) Continuation of application No. 10/007,109, filed on Nov. 19, 2001, now abandoned, which is a division of application No. 09/448,260, filed on Nov. 23, 1999, now Pat. No. 6,939,988, which is a division of application No. 09/012,585, filed on Jan. 23, 1998, now Pat. No. 6,054,453.

(30) Foreign Application Priority Data

Oct. 27, 1997  (IN)  ............................. 2416/MAS/97

(51) Int. Cl.
 *C07D 265/38*  (2006.01)
(52) U.S. Cl. .................................... 544/102
(58) Field of Classification Search ................ 544/102
 See application file for complete search history.

(56) References Cited

U.S. PATENT DOCUMENTS

| | | | |
|---|---|---|---|
| 5,104,888 A | 4/1992 | Yoshioka | 514/369 |
| 5,227,490 A | 7/1993 | Hartman | 514/317 |
| 5,306,726 A | 4/1994 | Hulin | 514/375 |
| 5,593,970 A | 1/1997 | Attardo et al. | |
| 5,622,948 A | 4/1997 | Dunn et al. | |
| 5,648,368 A | 7/1997 | Egbertson | 514/331 |
| 5,801,173 A | 9/1998 | Lohray et al. | 514/252 |
| 5,885,997 A | 3/1999 | Lohray et al. | 514/256 |
| 5,889,025 A | 3/1999 | Lohray et al. | 514/326 |
| 5,889,032 A | 3/1999 | Lohray et al. | 514/369 |
| 5,919,782 A | 7/1999 | Lohray et al. | 514/252 |
| 5,925,656 A | 7/1999 | Kallam et al. | 514/369 |
| 5,985,884 A | 11/1999 | Lohray et al. | 514/259 |
| 6,011,031 A | 1/2000 | Lohray et al. | 514/224.2 |
| 6,011,036 A | 1/2000 | Lohray et al. | 514/248 |
| 6,030,973 A | 2/2000 | Lohray et al. | 514/259 |
| 6,054,453 A | 4/2000 | Lohray et al. | 514/226.2 |
| 6,159,966 A | 12/2000 | Lohray et al. | 514/224.8 |
| 6,265,401 B1 | 7/2001 | Lohray et al. | 514/230.5 |
| 6,313,113 B1 | 11/2001 | Lohray et al. | 514/224.2 |
| 6,440,961 B1 | 8/2002 | Lohray et al. | |

FOREIGN PATENT DOCUMENTS

| | | |
|---|---|---|
| EP | 0441539 | 8/1991 |
| EP | 0903343 | 3/1999 |
| EP | 0916651 | 5/1999 |
| EP | 1026149 | 8/2000 |
| JP | 05194236 | 11/1993 |
| JP | 09012575 | 5/1997 |
| WO | 9119702 | 12/1991 |
| WO | 9401420 | 1/1994 |
| WO | 9413650 | 6/1994 |
| WO | 9517394 | 6/1995 |
| WO | 95/18793 | 7/1995 |
| WO | 9604260 | 2/1996 |
| WO | 9725042 | 7/1997 |
| WO | 9741097 | 11/1997 |
| WO | 00/26200 | 5/2000 |
| WO | 0140159 | 6/2001 |
| WO | 0140165 | 6/2001 |
| WO | 0140166 | 6/2001 |
| WO | 0140169 | 6/2001 |
| WO | 0140170 | 6/2001 |

(Continued)

OTHER PUBLICATIONS

Buckle, D.R. "Non Thiazolidinedione Antihyperglycaemic Agents . . ."Bioorganic & Medicinal Chemistry Letters vol. 6, No. 17, pp. 2121-2126, 1996.

(Continued)

*Primary Examiner*—Bruck Kifle
(74) *Attorney, Agent, or Firm*—Milagros A. Cepeda; Edward D. Pergament

(57) ABSTRACT

Novel β-aryl-α-oxysubstituted alkylcarboxylic acids of the formula (I) and compositions containing them.

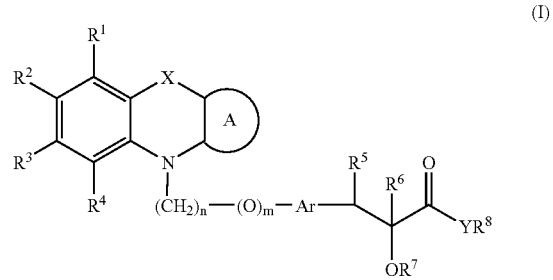

The compounds have hypolipidemic, antihyperglycemic uses.

1 Claim, No Drawings

FOREIGN PATENT DOCUMENTS

| WO | 0140171 | 6/2001 |
| --- | --- | --- |
| WO | 0140172 | 6/2001 |
| WO | 0153257 | 7/2001 |

OTHER PUBLICATIONS

Hulin, B. "Hypoglycemic Activity of A series of . . . "J. Med. Chem. 36, 1996, pp. 3897-3907.

Patent Abstracts of Japan vol. 97, No. 5, May 30, 1997 & JP 09 012575, Jan. 1997.

Patent Abstracts of Japan of JP 05 194236 dated Nov. 19, 1993, No. 627 (C11-3 vol. 17.

Lavelle et al., Chemical Abstracts, vol. 120:31084 (1994).

Attardo et al., Chemical Abstracts, vol. 117:27052 (1992).

Vanderhaeghe, et al. Journal of Organic Chemistry (1961) pp. 3827-3831.

CAS abstract AN 1994: 482641 of Tetrahedron Letters (1994), 35(19), 3139-42 in particular compounds RN 156335-15-8, RN 156335-16-9, RN 156335-21-6.

CAS abstract AN 1979: 438972 of Chemishe Berichte (1979), 112(5), 1571-84 in particular compound RN 70680-30-7.

CAS abstract AN 1972: 526535 of Tetrahedron Letters (1972), (29), 2911-14 in particular compound RN 38291-54-2.

TRICYCLIC COMPOUNDS AND THEIR USE IN MEDICINE; PROCESS FOR THEIR PREPARATION AND PHARMACEUTICAL COMPOSITIONS CONTAINING THEM

This is a continuation of application number application Ser. No. 10/007,109 filed on Nov. 19, 2001 now abandoned which is a divisional of application Ser. No. 09/448,260 filed Nov. 23, 1999 now U.S. Pat. No. 6,939,988, which is a divisional of application Ser. No. 09/012,585 filed Jan. 23, 1998 (now U.S. Pat. No. 6,054,453 issued on Apr. 23, 2000) claims the benefit thereof and incorporates the same by reference.

FIELD OF THE INVENTION

The present invention relates to novel hypolipidemic, antihyperglycemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of the general formula (I), their derivatives, their analogs, their tautomeric forms, their stereoisomers, their polymorphs, their pharmaceutically acceptable salts, their pharmaceutically acceptable solvates and pharmaceutically acceptable compositions containing them.

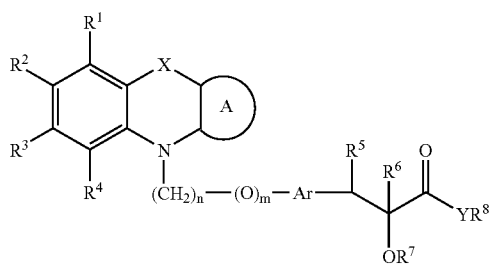
(I)

The present invention also relates to a process for the preparation of the above said novel compounds, their derivatives, their analogs, their tautomeric forms, their stereoisomers, their polymorphs, their pharmaceutically acceptable salts, pharmaceutically acceptable solvates, novel intermediates and pharmaceutical compositions containing them.

The compounds of general formula (I) are useful for the treatment and/or prophylaxis of insulin resistance (type 2 diabetes), impaired glucose tolerance, dyslipidemia, disorders related to Syndrome X such as hypertension, obesity, insulin resistance, atherosclerosis, hyperlipidemia, coronary artery disease and other cardiovascular disorders The compounds of the present invention are also useful for the treatment of certain renal diseases including glomerulonephritis, glomerulosclerosis, nephrotic syndrome, hypertensive nephrosclerosis. These compounds may also be useful as aldose reductase inhibitors, for improving cognitive functions in dementia, treating diabetic complications, psoriasis, polycystic ovarian syndrome (PCOS) and osteoporosis.

BACKGROUND OF INVENTION

Hyperlipidemia is the primary cause for cardiovascular disease (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown is that lowering of plasma triglycerides and total cholesterol, in particular LDL and VLDL and increasing HDL (High Density Lipoprotein) cholesterol help in preventing cardiovascular diseases.

Diabetes is a disease, which severely affects the quality of life of a large population. Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises resulting in frank diabetes. Among developed countries, diabetes mellitus is a common problem and is associated with a variety of abnormalities including obesity, hypertension, hyperlipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and renal complications (See Patent Application No. WO 95/21608). It is increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X.

Thus, therapeutic agents which improve insulin resistance, lower plasma triglycerides, total cholesterol, LDL and VLDL and increase HDL will have great significance in preventing cardiovascular morbidity and improving quality of life.

Peroxisome proliferator activated receptors (PPAR) are members of the nuclear receptor super family. The gamma (γ) isoform of PPAR (PPARγ) has been implicated in regulating differentiation of adipocytes (Endocrinology, (1994) 135: 798–800) and energy homeostasis (Cell, (1995) 83: 803–812), whereas the alpha (α) isoform of PPAR (PPARα) mediates fatty acid oxidation (Trend. Endocrin. Metab., (1993) 4: 291–296) thereby resulting in reduction of circulating free fatty acid in plasma (Current Biol. (1995) 68: 618–621). PPARα agonists have been found useful for the treatment of obesity (WO 97/36579). It has been recently disclosed that there exists synergism for the molecules, which are agonists for both PPARα and PPARγ and suggested to be useful for the treatment of syndrome X (WO 97/25042). Similar synergism between the insulin sensitizer (PPARγ agonist) and HMG CoA reductase inhibitor has been observed which may be useful for the treatment of atherosclerosis and xanthoma. (EP 0 753 298).

A few β-aryl-α-hydroxy propionic acids, their derivatives and their analogs have been reported to be useful in the treatment of hyperglycemia, hyperlipidemia and hypercholesterolemia. Some of such compounds described in the prior art are outlined below:

i) U.S. Pat. No. 5,306,726; WO91/19702 disclose several 3-aryl-2-hydroxypropionic acid derivatives of general formulas (IIa) and (IIb) as hypolipidemic and hypoglycemic agents.

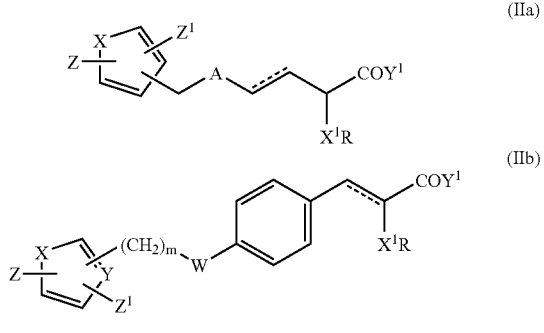

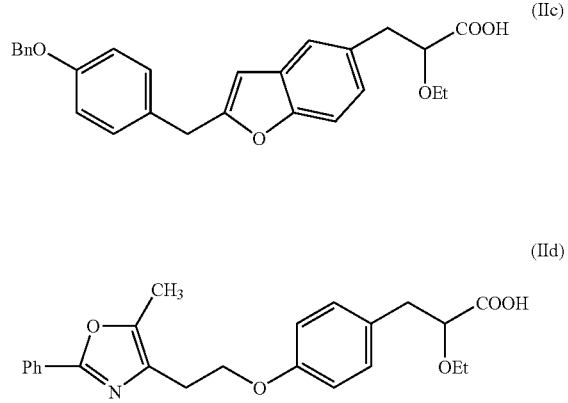

Examples of these compounds are shown in formulas (II c) and (II d)

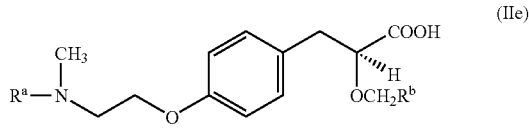

ii) International Patent Applications, WO 95/03038 and WO 96/04260 disclose compounds of formula (II e)

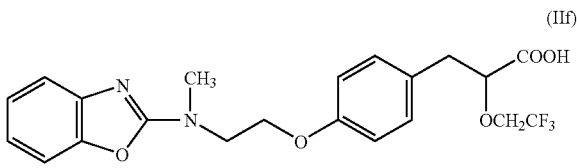

wherein $R^a$ represents 2-benzoxazolyl or 2-pyridyl and $R^b$ represents $CF_3$, $CH_2OCH_3$ or $CH_3$. A typical example is (S)-3-[4-[2-[N-(2-benzoxazolyl)N-methylamino]ethoxy]phenyl]-2-(2,2,2-trifluoroethoxy)propanoic acid (II f).

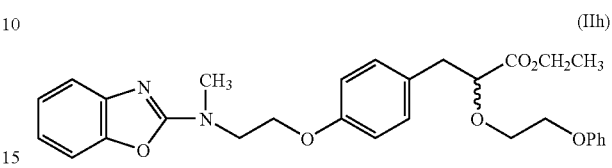

iii) International Patent Application Nos. WO 94/13650, WO 94/01420 and WO 95/17394 disclose the compounds of general formula (II g)

$A^1\text{-}(CH_2)_n\text{-}O\text{-}A^2\text{-}A^3\text{-}Y.R^2$  (II g)

wherein $A^1$ represents aromatic heterocycle, $A^2$ represents substituted benzene ring and $A^3$ represents moiety of formula $(CH_2)_m\text{-}CH\text{-}(OR^1)$, wherein $R^1$ represents alkyl groups, m is an integer; X represents substituted or unsubstituted N; Y represents C=O or C=S. $R^2$ represents $OR^3$ where $R^3$ may be alkyl, aralkyl, or aryl group. An example of these compounds is shown in formula (II h)

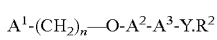

SUMMARY OF THE INVENTION

With an objective to develop novel compounds for the treatment and/or prophylaxis of diseases related to increased levels of lipids, especially to treat hypertriglyceridemia and to lower free fatty acids, for the treatment and/or prophylaxis of diseases described as Syndrome-X which include hyperlipidemia, hyperinsulinemia, obesity, insulin resistance, insulin resistance leading to type 2 diabetes and diabetes complications thereof, for the treatment of diseases wherein insulin resistance is the pathophysiological mechanism, for the treatment of hypertension, atherosclerosis and coronary artery diseases with better efficacy, potency and lower toxicity, we focussed our research to develop new compounds effective in the treatment of above mentioned diseases. Effort in this direction has led to compounds having general formula (I).

The main objective of the present invention is therefore, to provide novel β-aryl-α-oxysubstituted alkylcarboxylic acids and their derivatives, their analogs, their tautomeric forms, their stereoisomers, their polymorphs, their pharmaceutically acceptable salts, their pharmaceutically acceptable solvates and pharmaceutical compositions containing them, or their mixtures.

Another objective of the present invention is to provide novel β-aryl-α-oxysubstituted alkylcarboxylic acids and their derivatives, their analogs, their tautomeric forms, their stereoisomers, their polymorphs, their pharmaceutically acceptable salts, their pharmaceutically acceptable solvates and pharmaceutical compositions containing them or their mixtures which may have agonist activity against PPARα and/or PPARγ, and optionally inhibit HMG CoA reductase, in addition to agonist activity against PPARα and/or PPARγ.

Another objective of the present invention is to provide novel β-aryl-α-oxysubstituted alkylcarboxylic acids and their derivatives, their analogs, their tautomeric forms, their stereoisomers, their polymorphs, their pharmaceutically acceptable salts, their pharmaceutically acceptable solvates and pharmaceutical compositions containing them or their mixtures having enhanced activities, without toxic effect or with reduced toxic effect.

Yet another objective of the present invention is to produce a process for the preparation of novel β-aryl-α-oxysubstituted alkylcarboxylic acids and their derivatives of the formula (I) as defined above, their analogs, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their analogs, their derivatives, their tautomers, their stereoisomers, their polymorphs, their salts, solvates or their mixtures in combination with suitable carriers, solvents, diluents and other media normally employed in preparing such compositions.

DETAILED DESCRIPTION OF THE INVENTION

The present invention is related to compounds having the general formula (I)

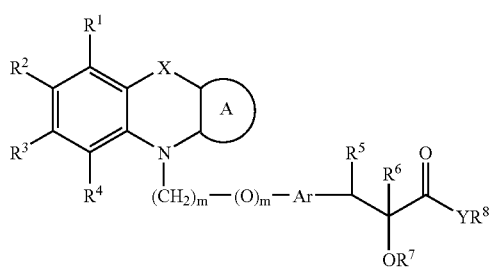

(I)

where $R^1$, $R^2$, $R^3$, and $R^4$ may be same or different and represent hydrogen, halogen, hydroxy, nitro, cyano, formyl or optionally substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, alkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; the ring A fused to the ring containing X and N represents a 5–6 membered cyclic structure containing carbon atoms, which may optionally contain one or more heteroatoms selected from oxygen, sulfur or nitrogen atoms, which may optionally be substituted; the ring A may be saturated or contain one or more double bonds or may be aromatic: X represents a heteroatom selected from oxygen, sulfur or $NR^9$ where $R^9$ is hydrogen alkyl, aryl, aralkyl, acyl, alkoxycarbonyl, aryloxycarbonyl, aralkoxycarbonyl and the like; Ar represents an optionally substituted divalent single or fused aromatic or heterocyclic group; $R^5$ represents hydrogen atom, hydroxy, alkoxy, halogen, lower alkyl, optionally substituted aralkyl group or forms a bond together with the adjacent group $R^6$; $R^6$ represents hydrogen, hydroxy, alkoxy, halogen, lower alkyl group, acyl, optionally substituted aralkyl or $R^6$ forms a bond together with $R^5$; $R^7$ represents hydrogen or optionally substituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl, or heteroaralkyl groups; $R^8$ may be hydrogen or optionally substituted groups selected from alkyl, cycloalkyl, aryl, aralkyl, heterocyclyl, heteroaryl, or heteroaralkyl groups; Y represents oxygen or $NR^{10}$, where $R^{10}$ represents hydrogen, alkyl, aryl, hydroxyalkyl or aralkyl groups; $R^8$ and $R^{10}$ together may form a 5 or 6 membered cyclic structure containing carbon atoms, which may optionally contain one or more heteroatoms selected from oxygen, sulfur or nitrogen; n is an integer ranging from 1–4 and m is an integer 0 or 1.

Suitable groups represented by $R^1$–$R^4$ include hydrogen, halogen atom such as fluorine, chlorine, bromine, or iodine; hydroxy, cyano, nitro, formyl; substituted or unsubstituted $(C_1-C_{12})$alkyl group, especially, linear or branched $(C_1-C_6)$ alkyl group, such as methyl, ethyl, n-propyl, isopropyl, n-butyl, iso-butyl, t-butyl, n-pentyl, isopentyl, hexyl and the like; cyclo$(C_3-C_6)$alkyl group such as cyclopropyl, cyclobutyl, cyclopentyl, cyclohexyl and the like, the cycloalkyl group may be substituted; cyclo$(C_3-C_6)$alkyloxy group such as cyclopropyloxy, cyclobutyloxy, cyclopentyloxy, cyclohexyloxy and the like, the cycloalkoxy group may be substituted; aryl group such as phenyl, naphthyl and the like, the aryl group may be substituted; aralkyl such as benzyl or phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heterocyclyl groups such as aziridinyl, pyrrolidinyl, morpholinyl, piperidinyl, piperazinyl and the like, the heterocyclyl group may be substituted; aralkoxy group such as benzyloxy, phenethyloxy, naphthylmethyloxy, phenylpropyloxy and the like, the aralkoxy group may be substituted; heteroaralkyl group such as furanmethyl, pyridinemethyl, oxazolemethyl, oxazolethyl and the like, the heteroaralkyl group may be substituted; aralkylamino group such as $C_6H_5CH_2NH$, $C_6H_5CH_2CH_2NH$, $C_6H_5CH_2NCH_3$ and the like, which may be substituted; aralkoxycarbonyl group such as benzyloxycarbonyl, phenethyloxycarbonyl, naphthylmethoxycarbonyl and the like, which may be substituted; $(C_1-C_6)$alkylamino group such as $NHCH_3$, $N(CH_3)_2$, $NCH_3(C_2H_5)$, $NHC_2H_5$, $NHC_3H_7$, $NHC_6H_{13}$ and the like; alkoxyalkyl group such as methoxymethyl, ethoxymethyl, methoxyethyl, ethoxyethyl and the like; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; heteroaryloxy and heteroaralkoxy, wherein heteroaryl moiety is as defined earlier and may be substituted; aryloxy group such as phenoxy, naphthyloxy and the like; the aryloxy group may be substituted; alkoxycarbonyl such as methoxycarbonyl, ethoxycarbonyl and the like; aryloxycarbonyl group such as optionally substituted phenoxycarbonyl, naphthyloxycarbonyl and the like; arylamino group such as $HNC_6H_5$, $NCH_3(C_6H_5)$, $NHC_6H_4CH_3$, $NHC_6H_4$-Hal and the like; amino group; amino$(C_1-C_6)$alkyl; hydroxy $(C_1-C_6)$alkyl; $(C_1-C_6)$alkoxy such as methoxy, ethoxy, propyloxy, butyloxy, iso-propyloxy and the like; thio$(C_1-C_6)$alkyl; $(C_1-C_6)$alkylthio; acyl group such as acetyl, propionyl, benzoyl and the like, the acyl group may be substituted; acylamino groups such as $NHCOCH_3$, $NHCOC_2H_5$, $NHCOC_3H_7$, $NHCOC_6H_5$ and the like; aralkoxycarbonylamino group such as $NHCOOCH_2C_6H_5$, $NHCOOCH_2CH_2C_6H_5$, $NCH_3COOCH_2C_6H_5$, $NC_2H_5COOCH_2C_6H_5$, $NHCOOCH_2C_6H_4CH_3$, $NHCOOCH_2C_6H_4OCH_3$ and the like; aryloxycarbonylamino group such as $NHCOOC_6H_5$, $NHCOOC_6H_5$, $NCH_3COOC_6H_5$, $NC_2H_5COOC_6H_5$, $NHCOOC_6H_4CH_3$, $NHCOOC_6H_4OCH_3$ and the like; alkoxycarbonylamino group such as $NHCOOC_2H_5$, $NHCOOCH_3$ and the like; carboxylic acid or its derivatives such as amides, like $CONH_2$, $CONHMe$, $CONMe_2$, $CONHEt$, $CONEt_2$, $CONHPh$ and the like, the carboxylic acid derivatives may be substituted; acyloxy group such as OOCMe, OOCEt, OOCPh and the like which may optionally be substituted; sulfonic acid or its derivatives such as $SO_2NH_2$, $SO_2NHMe$, $SO_2NMe_2$, $SO_2NHCF_3$ and the like, the sulfonic acid derivatives may be substituted.

When the groups represented by $R^1$–$R^4$ are substituted, the substituents may be selected from halogen, hydroxy, or nitro or optionally substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives.

Suitable ring A includes phenyl, naphthyl, cyclohexyl, cyclohexenyl, thienyl, furyl, pyrrolyl, oxazolyl, oxadiazolyl, thiazolyl, imidazolyl, isoxazolyl, pyridyl, pyranyl, dihydropyranyl, pyridazyl, pyrimidinyl and the like; which may be optionally substituted and substituents are selected from the same group as that of $R^1$–$R^4$ and are defined as they are for $R^1$–$R^4$. Preferred substituents are halogen, hydroxy, amino, formyl, optionally halogenated $(C_1–C_6)$alkyl, $(C_1–C_6)$alkoxy, cyclo$(C_3–C_6)$alkyl, cyclo$(C_3–C_6)$alkoxy, aryl, aralkyl, aralkoxy, heterocyclyl, acyl, acyloxy, carboxyl, alkoxycarbonyl, aralkoxycarbonyl, alkylamino, acylamino, aralkoxycarbonylamino, aminocarbonyl and the like.

It is preferred that cyclic structure represented by ring A is a phenyl or a pyridyl ring.

It is still more preferred that the cyclic structure represented by ring A is a phenyl ring.

Suitable X includes oxygen, sulfur or a group $NR^9$, preferably oxygen and sulfur. Suitably, $R^9$ represents hydrogen, $(C_1–C_6)$alkyl, $(C_3–C_6)$cycloalkyl, aralkyl group such as benzyl, phenethyl; acyl group such as acetyl, propanoyl, butanoyl, benzoyl and the like; $(C_1–C_6)$alkoxycarbonyl; aryloxycarbonyl such as phenoxycarbonyl, $CH_3OC_6H_4OCO$, Hal-$C_6H_4OCO$, $CH_3C_6H_4OCO$, naphthyloxycarbonyl and the like; aralkoxycarbonyl such as benzyloxycarbonyl, phenethyloxycarbonyl and the like; the groups represented by $R^9$ may be substituted or unsubstituted. When the groups represented by $R^9$ are substituted, the substituents may be selected from halogen, optionally halogenated lower alkyl, hydroxy, and optionally halogenated $(C_1–C_3)$alkoxy groups.

The group represented by Ar includes divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl, pyrazolyl and the like. The substituents on the group represented by Ar include linear or branched optionally halogenated $(C_1–C_6)$alkyl, optionally halogenated $(C_1–C_3)$alkoxy, halogen, acyl, amino, acylamino, thio, carboxylic and sulfonic acids and their derivatives. The substituents are defined as they are for $R^1$–$R^4$.

It is more preferred that Ar represents a substituted or unsubstituted divalent phenylene, naphthylene, benzofuranyl, indolyl, indolinyl, quinolinyl, azaindolyl, azaindolinyl, benzothiazolyl or benzoxazolyl group.

It is still more preferred that Ar represents divalent phenylene or benzofuranyl, which may be optionally substituted by methyl, halomethyl, methoxy or halomethoxy groups.

Suitable $R^5$ includes hydrogen, lower alkyl groups such as methyl, ethyl or propyl; hydroxy, $(C_1–C_3)$alkoxy; halogen atom such as fluorine, chlorine, bromine, iodine; aralkyl such as benzyl, phenethyl, which may be optionally substituted or $R^5$ together with $R^6$ represent a bond.

Suitable $R^6$ may be hydrogen, lower alkyl groups such as methyl, ethyl or propyl; hydroxy, $(C_1–C_3)$alkoxy; halogen atom such as fluorine, chlorine, bromine, iodine; acyl group such as linear or branched $(C_1–C_9)$acyl group such as acetyl, propanoyl, butanoyl, pentanoyl, benzoyl and the like; aralkyl such as benzyl, phenethyl, which may be optionally substituted or $R^6$ together with $R^5$ forms a bond.

It is preferred that $R^5$ and $R^6$ represent hydrogen atoms or $R^5$ and $R^6$ together represent a bond.

Suitable groups represented by $R^7$ may be selected from hydrogen, linear or branched $(C_1–C_{16})$alkyl, preferably $(C_1–C_{12})$alkyl group such as methyl, ethyl, n-propyl, iso-propyl, n-butyl, iso-butyl, pentyl, hexyl, octyl and the like: $(C_3–C_7)$cycloalkyl group Such as cyclopropyl, cyclobutyl, cyclopentyl, cyclohexyl, and the like, the cycloalkyl group may be substituted; aryl group such as phenyl, naphtyl and the like, the aryl group may be substituted; heteroaryl group such as pyridyl, thienyl, furyl and the like, the heteroaryl group may be substituted; heteroaralkyl group such as furanmethyl, pyridinemethyl, oxazolemethyl, oxazolethyl and the like, the heteroaralkyl group may be substituted; aralkyl group wherein the alkyl moiety may contain $C_1–C_6$ atoms such as benzyl and phenethyl etc, wherein the aryl moiety may be substituted; heterocyclyl group such as aziridinyl, pyrrolidinyl, piperidinyl and the like, the heterocyclyl group may be substituted; $(C_1–C_6)$alkoxy$(C_1–C_6)$ alkyl group such as methoxymethyl, ethoxymethyl, methoxyethyl, ethoxypropyl and the like, the alkoxyalkyl group may be substituted; acyl group such as acetyl, propanoyl, butanoyl, benzoyl and the like; $(C_1–C_6)$alkoxycarbonyl, the alkyl group may be substituted; aryloxycarbonyl such as phenoxycarbonyl, naphthyloxycarbonyl and the like, the aryl group may be substituted; $(C_1–C_6)$alkylaminocarbonyl, the alkyl group may be substituted; arylaminocarbonyl such as PhNHCO, naphthylaminocarbonyl and the like, the aryl moiety may be substituted. The substituents on $R^7$ may be selected from the same group as $R^1$–$R^4$ and are defined in the same way.

Suitable groups represented by $R^8$ may be selected from hydrogen, linear or branched $(C_1–C_{16})$alkyl, preferably $(C_1–C_{12})$alkyl group such as methyl, ethyl, n-propyl, iso-propyl, n-butyl, iso-butyl, pentyl, hexyl, octyl and the like; $(C_3–C_7)$cycloalkyl such as cyclopropyl, cyclopentyl, cyclohexyl and the like, the cycloalkyl group may be substituted; aryl group such as phenyl, naphthyl and the like, the aryl group may be substituted; heteroaryl group such as pyridyl, thienyl, furyl and the like, the heteroaryl group may be substituted; heteroaralkyl group such as furanmethyl, pyridinemethyl, oxazolemethyl, oxazolethyl and the like, the heteroaralkyl group may be substituted; aralkyl group such as benzyl, phenethyl and the like, the aralkyl group may be substituted; heterocyclyl group such as aziridinyl, pyrrolidinyl, piperidinyl and the like, the heterocyclyl group may be substituted. The substituents on $R^8$ may be selected from the same group of $R^1$–$R^4$.

Suitable groups represented by $R^{10}$ may be selected from hydrogen, linear or branched $(C_1–C_{16})$alkyl, preferably $(C_1–C_{12})$alkyl; hydroxy$(C_1–C_6)$alkyl; aryl group such as phenyl, naphthyl; aralkyl group such as benzyl and phenethyl.

Suitable ring structures formed by $R^8$ and $R^{10}$ together may be selected front pyrrolidinyl, piperidinyl, morpholinyl, piperazinyl and the like.

Suitable m is an integer ranging from 0–1. It is preferred that when m=0 Ar represents a divalent benzofuranyl, benzoxazolyl, benzothiazolyl, indolyl, indolinyl, dihydrobenzofuryl, or dihydrobenzopyranyl group, preferably benzofuranyl group and when m=1, Ar represents divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl, or pyrazolyl group.

It is preferred that when m=0, Ar represents a divalent benzofuranyl group, more preferably benzofuran-2,5-diyl group, and when m=1, Ar represents a phenylene group.

Suitable n is an integer ranging from 1 to 4, preferably n represents an integer 1 or 2.

It is preferred that when m=1, n represents 2.

It is also preferred that when n=0, n represents 1.

Pharmaceutically acceptable salts forming part of this invention include salts of the carboxylic acid moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glyceroposphates, ketoglutarates and the like. Pharmaceutically acceptable solvates may be hydrates or comprising other solvents of crystallization such as alcohols.

Particularly useful compounds according to the present invention include

Ethyl (E/Z)-3-[4-[2-(phenothiazin-10-yl)ethoxy]phenyl]-2-ethoxy propenoate and its salts;

Ethyl (E)-3-[4-[2-(phenothiazin-10-yl)ethoxy]phenyl]-2-ethoxy propenoate and its salts;

Ethyl (Z)-3-[4-[2-(phenothiazin-10-yl)ethoxy]phenyl]-2-ethoxy propenoate and its salts;

Ethyl (E/Z)-3-[4-[2-[phenothiazin-10-yl)methylbenzofuran-5-yl]-2-ethoxypropenoate and its salts;

Ethyl(E)-3-[4-[2-[phenothiazin-10-yl)methylbenzofuran-5-yl]-2-ethoxypropenoate and its salts;

Ethyl(Z)-3-[4-[2-[phenothiazin-10-yl)methylbenzofuran-5-yl]-2-ethoxypropenoate and its salts;

Ethyl (E/Z)-3-[4-[2-(phenoxazin-10-yl)ethoxy]phenyl]-2-ethoxypropenoate and its salts;

Ethyl (E)-3-[4-[2-(phenoxazin-10-yl)ethoxy]phenyl]-2-ethoxypropenoate and its salts;

Ethyl (Z)-3-[4-[2-(phenoxazin-10-yl)ethoxy]phenyl]-2-ethoxypropenoate and its salts;

(±) Methyl 3-[4-[2-(phenothiazin-10-yl)ethoxy]phenyl]-2-ethoxypropanoate and its salts;

(+) Methyl 3-[4-[2-(phenothiazin-10-yl)ethoxy]phenyl]-2-ethoxypropanoate and its salts;

(−) Methyl 3-[4-[2-(phenothiazin-10-yl)ethoxy]phenyl]-2-ethoxypropanoate and its salts;

(±) Methyl 3-[2-(phenothiazin-10-yl)methylbenzofuran-5-yl]-2-ethoxypropanoate and its salts;

(+) Methyl 3-[2-(phenothiazin-10-methylbenzofuran-5-yl]-2-ethoxypropanoate and its salts;

(−) Methyl 3-[2-(phenothiazin-10-yl)methylbenzofuran-5-yl]-2-ethoxypropanoate and its salts;

(±) Methyl 3-[4-[2-(phenoxazin-10-yl)ethoxy]phenyl]-2-ethoxypropanoate and its salts;

(+) Methyl 3-[4-[2-(phenoxazin-10-yl)ethoxy]phenyl]-2-ethoxypropanoate and its salts;

(−) Methyl 3-[4-[2-(phenoxazin-10-yl)ethoxy]phenyl]-2-ethoxypropanoate and its salts;

(±) Ethyl 3-[4-(2-(phenoxazin-10-yl)ethoxy]phenyl-2-ethoxypropanoate and its salts;

(+) Ethyl 3-[4-(2-(phenoxazin-10-yl)ethoxy]phenyl-2-ethoxypropanoate and its salts;

(−) Ethyl 3-[4-(2-(phenoxazin-10-yl)ethoxy]phenyl-2-ethoxypropanoate and its salts;

(±) Ethyl 3-[4-[2-(phenoxazin-10-yl)ethoxy]phenyl]-2-hydroxypropanoate and its salts;

(+) Ethyl 3-[4-[2-(phenoxazin-10-yl)ethoxy]phenyl]-2-hydroxypropanoate and its salts;

(−) Ethyl 3-[4-[2-(phenoxazin-10-yl)ethoxy]phenyl]-2-hydroxypropanoate and its salts;

(±) Ethyl 3-[4-[2-(phenoxazin-10-yl)ethoxy]phenyl]-2-butoxypropanoate and its salts;

(+) Ethyl 3-[4-[2-(phenoxazin-10-yl)ethoxy]phenyl]-2-butoxypropanoate and its salts;

(−) Ethyl 3-[4-[2-(phenoxazin-10-yl)ethoxy]phenyl]-2-butoxypropanoate and its salts;

(±) Ethyl 3-[4-[2-(phenoxazin-10-yl)ethoxy]phenyl]-2-hexyloxypropanoate and its salts;

(−) Ethyl 3-[4-[2-(phenoxazin-10-yl)ethoxy]phenyl]-2-hexyloxypropanoate and its salts;

(−) Ethyl 3-[4-[2-(phenoxazin-10-yl)ethoxy]phenyl]-2-hexyloxypropanoate and its salts;

(±) 3-[4-[2-(phenothiazin-10-yl)ethoxy]phenyl]-2-ethoxypropanoic acid and its salts;

(+) 3-[4-[2-(phenothiazin-10-yl)ethoxy]phenyl]-2-ethoxypropanoic acid and its salts;

(−) 3-[4-[2-(phenothiazin-10-yl)ethoxy]phenyl]-2-ethoxypropanoic acid and its salts;

(±) 3-[4-[2-(phenothiazin-10-yl)ethoxy]phenyl]-2-ethoxy-2-methylpropanoic acid and its salts;

(+) 3-[4-[2-(phenothiazin-10-yl)ethoxy]phenyl]-2-ethoxy-2-methylpropanoic acid and its salts;

(−) 3-[4-[2-(Phenothiazin-10-yl)ethoxy]phenyl]-2-ethoxy-2-methylpropanoic acid and its salts;

(±) 3-[4-[2-(Phenothiazin-10-yl)ethoxy]phenyl]-2-phenoxypropanoic acid and its salts;

(+) 3-[4-[2-(Phenothiazin-10-yl)ethoxy]phenyl]-2-phenoxypropanoic acid and its salts;

(−) 3-[4-[2-(Phenothiazin-10-yl)ethoxy]phenyl]-2-phenoxypropanoic acid and its salts;

(±) 3-[4-[2-(Phenothiazin-10-yl)ethoxy]phenyl]-2-phenoxy-2-methylpropanoic acid and its salts;

(+) 3-[4-[2-(Phenothiazin-10-yl)ethoxy]phenyl]-2-phenoxy-2-methylpropanoic acid and its salts;

(−) 3-[4-[2-(Phenothiazin-10-yl)ethoxy]phenyl]-2-phenoxy-2-methylpropanoic acid and its salts;

(±) 3-[2-(Phenothiazin-10-yl)methyl benzofuran-5-yl]-2-ethoxypropanoic acid and its salts;

(+) 3 [2-(Phenothiazin-10-yl)methyl benzofuran-5-yl]-2-ethoxypropanoic acid and its salts;

(−) 3-[2-(Phenothiazin-10-yl)methyl benzofuran-5-yl]-2-ethoxypropanoic acid and its salts;

(±) 3-[4-[2-(Phenoxazin-10-yl)ethoxy]phenyl]-2-ethoxypropanoic acid and its salts;

(+) 3-[4-[2-(Phenoxazin-10-yl)ethoxy]phenyl]-2-ethoxypropanoic acid and its salts;

(−) 3-[4-[2-(Phenoxazin-10-yl)ethoxy]phenyl]-2-ethoxypropanoic acid and its salts;

(±) 3-[4-[2-(Phenoxazin-10-yl)ethoxy]phenyl]-2-ethoxy-2-methylpropanoic acid and its salts;

(+) 3-[4-[2-(Phenoxazin-10-yl)ethoxy]phenyl]-2-ethoxy-2-methylpropanoic acid and its salts;

(−) 3-[4-[2-(Phenoxazin-10-yl)ethoxy]phenyl]-2-ethoxy-2-methylpropanoic acid and its salts;

(±) 3-[4-[2-(Phenoxazin-10-yl)ethoxy]phenyl]-2-phenoxypropanoic acid and its salts;

(+) 3-[4-[2-(Phenoxazin-10-yl)ethoxy]phenyl]-2-phenoxypropanoic acid and its salts;

(−) 3-[4-[2-(Phenoxazin-10-yl)ethoxy]phenyl]-2-phenoxypropanoic acid and its salts;

(±) 3-[4-[2-(Phenoxazin-10-yl)ethoxy]phenyl]-2-phenoxy-2-methylpropanoic acid and its salts;

(+) 3-[4-[2-(Phenoxazin-10-yl)ethoxy]phenyl]-2-phenoxy-2-methylpropanoic acid and its salts;

(−) 3-[4-[2-(Phenoxazin-10-yl)ethoxy]phenyl]-2-phenoxy-2-methylpropanoic acid and its salts;

(±) 3-[4-[2-(Phenoxazin-10-yl)ethoxy]phenyl]-2-hydroxypropanoic acid and its salts;

(+) 3-[4-[2-(Phenoxazin-10-yl)ethoxy]phenyl]-2-hydroxypropanoic acid and its salts;

(−) 3-[4-[2-(Phenoxazin-10-yl)ethoxy]phenyl]-2-hydroxypropanoic acid and its salts;

(±) 3-[4-[2-(Phenoxazin-10-yl)ethoxy]phenyl]-2-butoxypropanoic acid and its salts;

(+) 3-[4-[2-(Phenoxazin-10-yl)ethoxy]phenyl]-2-butoxypropanoic acid and its salts;

(−) 3-[4-[2-(Phenoxazin-10-yl)ethoxy]phenyl]-2-butoxypropanoic acid and its salts;

(±) 3-[4-[2-(Phenoxazin-10-yl)ethoxy]phenyl]-2-hexyloxypropanoic acid and its salts;

(+) 3-[4-[2-(Phenoxazin-10-yl)ethoxy]phenyl]-2-hexyloxypropanoic acid and its salts;

(−) 3-[4-[2-(Phenoxazin-10-yl)ethoxy]phenyl]-2-hexyloxypropanoic acid and its salts;

[(2R)-N(1S)]-3-[4-[2-(Phenoxazin-10-yl)ethoxy]phenyl]-2-ethoxy-N-(2-hydroxy-1-phenyl ethyl)propanamide and its salts;

[(2S)-N(1S)]-3-[4-[2-(Phenoxazin-10-yl)ethoxy]phenyl]-2-ethoxy-N-(2-hydroxy-1-phenyl ethyl)propanamide and its salts;

[(2S)-N(1S)]-3-[4-[2-(Phenothiazin-10-yl)ethoxy]phenyl]-2-ethoxy-N-(2-hydroxy-1-phenyl ethyl)propanamide and its salts; and

[(2R)-N(1S)]-3-[4-[2-(Phenothiazin-10-yl)ethoxy]phenyl]-2-ethoxy-N-(2-hydroxy-1-phenyl ethyl)propanamide and its salts.

According to a feature of the present invention, the compound of general formula (III) where $R^1$, $R^2$, $R^3$, $R^4$, $R^7$, $R^8$, X, A, n, m, Ar are as defined earlier and $R^5$ and $R^6$ together represent a bond can be prepared by any of the following routes shown in Scheme I. The compound of general formula (III) represents a compound of general formula (I), wherein all the symbols are as defined earlier and $R^5$ and $R^6$ together represent a bond and Y represents oxygen atom.

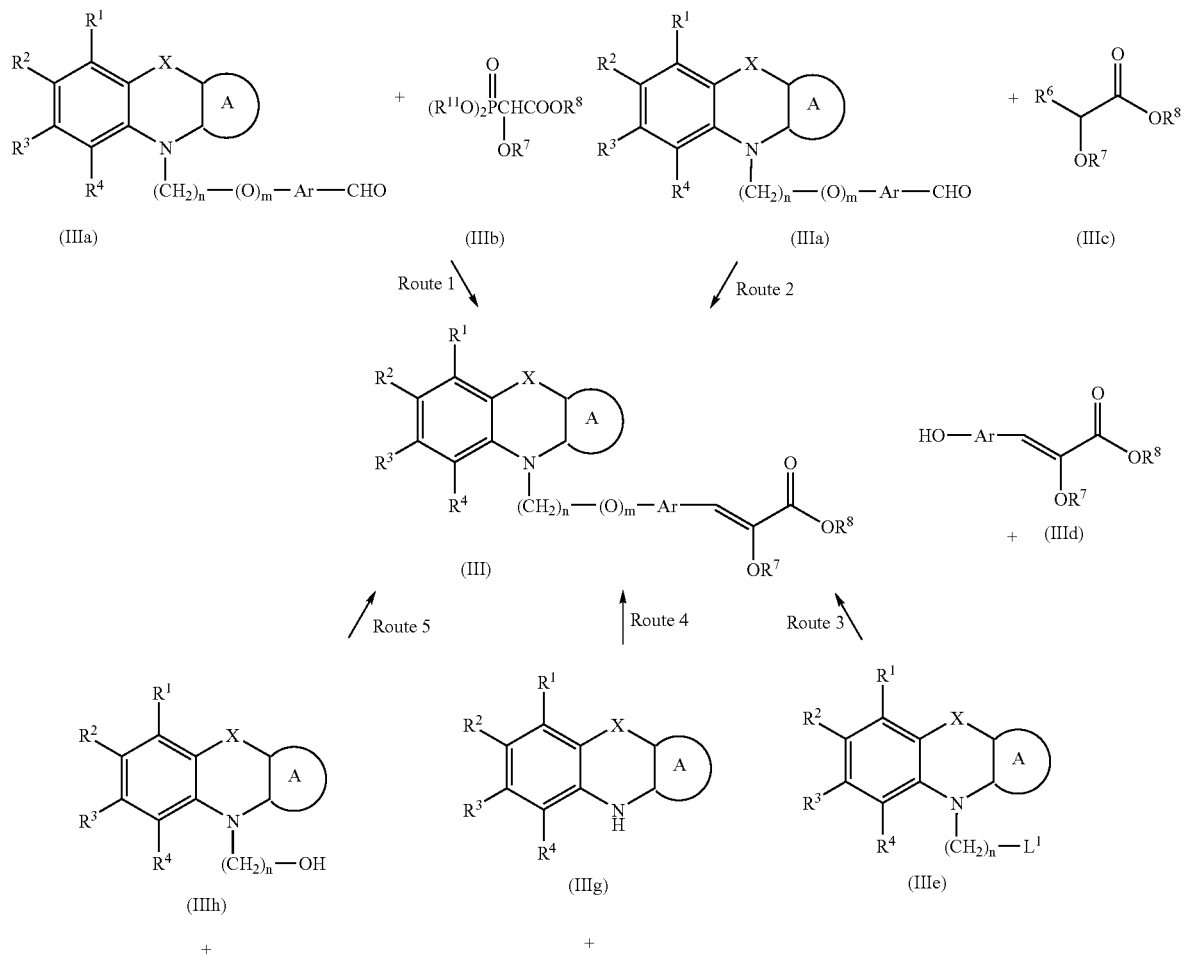

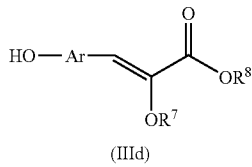 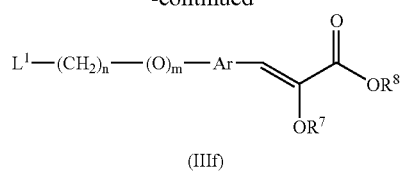

(IIId)                          (IIIf)

Route (1): The reaction of a compound of the general formula (IIIa) where all symbols are as defined earlier with a compound of formula (IIIb), where $R^{11}$ may be a lower alkyl group and $R^7$, $R^8$ are as defined earlier, to yield a compound of general formula (III) may be carried out in the presence of a base such as alkali metal hydrides like NaH, KH or organolithiums like $CH_3Li$, BuLi and the like or alkoxides such as NaOMe, NaOEt, $K^+BuO^-$ or mixtures thereof. The reaction may be carried out in presence of solvents such as THF, dioxane, DMF, DMSO, DME and the like or mixtures thereof. HMPA may be used as cosolvent. The reaction temperature may range from $-78°$ C. to $50°$ C., preferably at a temperature in the range of $-10°$ C. to $30°$ C. The compound of general formula (III b) may be prepared according to the procedure described in the literature (Annalen. Chemie, (1996) 53, 699).

Route (2): The reaction of a compound of the general formula (IIIa) where all symbols are as defined earlier with a compound of formula (IIIc) where $R^6$ represents a hydrogen atom and $R^7$, $R^8$ are as defined earlier may be carried out under conventional conditions. The base is not critical. Any base normally employed for aldol condensation reaction may be employed; bases like metal hydride such as NaH, or KH, metal alkoxides such as NaOMe, $K^+BuO^-$, NaOEt; metal amides such as $LiNH_2$, $LiN(ipr)_2$ may be used. Aprotic solvent such as THF, ether, dioxane may be used. The reaction may be carried out in an inert atmosphere which may be maintained by using inert gases such as $N_2$, Ar, or He and the reaction is more effective under anhydrous conditions. Temperature in the range of $-80°$ C. to $35°$ C. may be used. The β-hydroxy product may be dehydrated under conventional dehydration conditions such as treating with PTSA in solvents such as benzene or toluene. The nature of solvent and dehydrating agent is not critical. Temperature in the range of $20°$ C. to reflux temperature of the solvent used may be employed, preferably at reflux temperature of the solvent by continous removal of water using a Dean Stark water separator.

Route (3): The reaction of compound of formula (IIIe) where $L^1$ is a leaving group such as halogen atom, p-toluenesulfonate, methanesulfonate, trifluoromethanesulfonate and the like and all symbols are as defined earlier with a compound of formula (IIId) where $R^7$, $R^8$ and Ar are as defined earlier to produce a compound of the formula (III) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from $0°$ C.$-120°$ C., preferably at a temperature in the range of $30°$ C.$-100°$ C. The duration of the reaction may range from 1 to 24 hours, preferably from 2 to 12 hours. The compound of formula (IIId) can be prepared according to known procedure by a Wittig Horner reaction between the hydroxy protected aryl aldehyde such as benzyloxyaryl aldehyde and compound of formula (IIIb), followed by deprotection.

Route (4): The reaction of a compound of general formula (IIIg) where all symbols are as defined earlier with a compound of general formula (IIIf) where all symbols are as defined earlier and $L^1$ is a leaving group such as halogen atom, p-toluenesulfonate, methanesulfonate, trifluoromethanesulfonate and the like, preferably a halogen atom to produce a compound of general formula (III) may be carried out in the presence of solvents such as DMSO, DMF, DME, THF, dioxane, ether and the like or a combination thereof. The reaction may be carried out in an inert atmosphere which may be maintained by using inert gases such as $N_2$, Ar, or He. The reaction may be effected in the presence of a base such as alkalis like sodium hydroxide, potassium hydroxide, alkali metal carbonates like sodium carbonate, potassium carbonate; alkali metal hydrides such as sodium hydride or potassium hydride; organometallic bases like n-butyl lithium, alkali metal amides like sodamide or mixtures of bases. The amount of base may range from 1 to 5 equivalents, based on the amount of the compound of formula (IIIa), preferably the amount of base ranges from 1 to 3 equivalents. Phase transfer catalysts such as tetraalkylammonium halide or hydroxide may be added. The reaction may be carried out at a temperature in the range of $0°$ C. to $150°$ C., preferably at a temperature in the range of $15°$ C. to $100°$ C. The duration of the reaction may range from 0.25 to 48 hours, preferably from 0.25 to 12 hours.

Route (5): The reaction of compound of general formula (IIIh) where all symbols are as defined earlier with a compound of general formula (IIId) may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, or He. The reaction may be effected in the presence of DMAP, HOBT and they may be used in the range of 0.05 to 2 equivalents, preferably 0.25 to 1 equivalents. The reaction temperature may be in the range of $0°$ C. to $100°$ C., preferably at a temperature in the range of $20°$ C. to $80°$ C. The duration of the reaction may range from 0.5 to 24 hours, preferably from 6 to 12 hours.

According to another embodiment of the present invention, the compound of the general formula (I) where $R^1$, $R^2$, $R^3$, $R^4$, $R^5$, $R^6$, $R^7$, $R^8$, X, A, n, m, and Ar are as defined earlier and Y represents oxygen atom can be prepared by one or more of the processes shown in Scheme-II:

Scheme-II
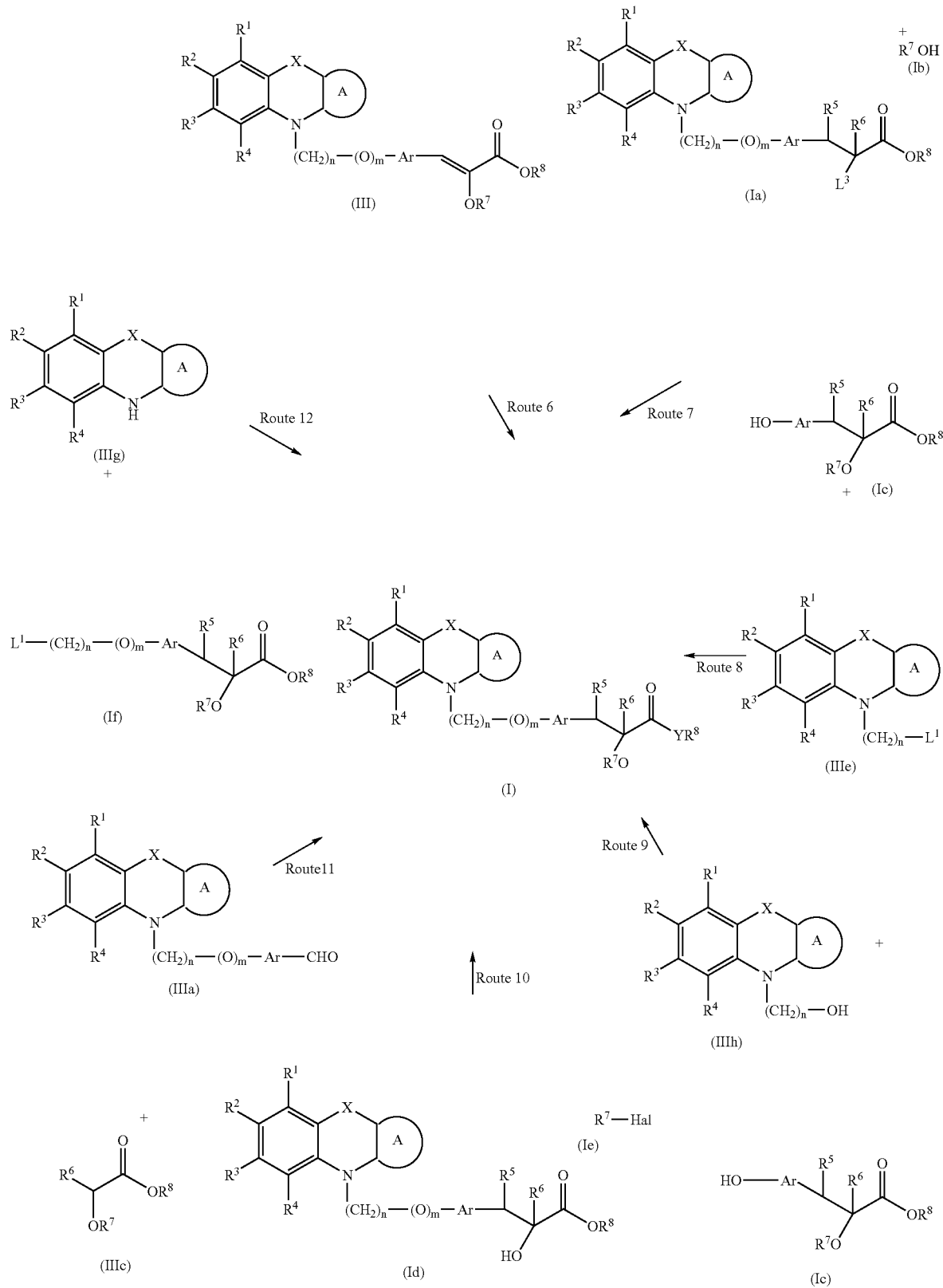

Route (6): The reduction of compound of the formula (III) obtained as described earlier in Scheme-I, to yield a compound of the general formula (I) where $R^5$ and $R^6$ each represent hydrogen atom and all symbols are as defined earlier, may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate, ethanol and the like. The nature of the solvent is not critical. A pressure between atmospheric pressure and 80 psi may be employed. Higher pressures may be used to reduce the reaction time. The catalyst may be preferably 5–10% Pd/C and the amount of catalyst used may range from 1–100% w/w. The reaction may also be carried out by employing metal solvent reduction such as magnesium in alcohol or sodium amalgam in alcohol.

Route (7): The reaction of compound of formula (Ia) where all symbols are as defined earlier and $L^3$ is a leaving group such as halogen atom with an alcohol of general formula (Ib), where $R^7$ is as defined earlier to produce a compound of the formula (I) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as KOH, NaOH, NaOMe, NaOEt, $K^+BuO^-$ or NaH or mixtures thereof. Phase transfer catalysts such as tetraalkylammonium halides or hydroxides may be employed. The reaction temperature may range from 20° C.–120° C., preferably at a temperature in the range of 30° C.–100° C. The duration of the reaction may range from 1 to 12 hours, preferably from 2 to 6 hours. The compound of formula (Ia) may be prepared according to the process disclosed in our copending application Ser. No. 08/982,910.

Route (8): The reaction of compound of formula (IIIe) defined earlier with compound of formula (Ic) where all symbols are as defined earlier to produce a compound of the formula (I) may be carried out in the presence of solvents such as THF, DMF, DMSO, DME and the like or mixtures thereof. The reaction may be carried out in an inert atmosphere which is maintained by using inert gases such as $N_2$, Ar or He. The reaction may be effected in the presence of a base such as $K_2CO_3$, $Na_2CO_3$ or NaH or mixtures thereof. Acetone may be used as a solvent when $K_2CO_3$ or $Na_2CO_3$ is used as a base. The reaction temperature may range from 20° C.–120° C., preferably at a temperature in the range of 30° C.–80° C. The duration of the reaction may range from 1 to 24 hours, preferably from 2 to 12 hours. The compound of formula (Ic) may be prepared by Wittig Homer reaction between the protected hydroxyaryl aldehyde and compound of formula (IIIb) followed by reduction of the double bond and deprotection. Alternatively, the compound of formula (Ic) may be prepared by following a procedure disclosed in WO 94/01420.

Route 9: The reaction of compound of general formula (IIIh) defined earlier with a compound of general formula (Ic) where all symbols are as defined earlier may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route (10): The reaction of compound of formula (Id) where all symbols are as defined earlier with a compound of formula (Ie) where $R^7$ is as defined earlier and Hal represents Cl, Br, or I, to produce a compound of formula (I) may be carried out in the presence of solvents such as THF, DMF, DMSO, DME and the like. The inert atmosphere may be maintained by using inert gases such as $N_2$, Ar or He. The reaction may be effected in the presence of a base such as KOH, NaOH, NaOMe, $K^+BuO^-$, NaH and the like. Phase transfer catalyst such as tetraalkylammonium halides or hydroxides may be employed. The reaction temperature may range from 20° C. to 150° C., preferably at a temperature in the range of 30° C. to 100° C. The duration of the reaction may range from 1 to 24 hours, preferably from 2 to 12 hours. The compound of formula (Id) represents compound of formula (I) where $R^7$ represents H and Y represents oxygen atom.

Route (11): The reaction of a compound of the general formula (IIIa) as defined earlier with a compound of formula (IIIc) where $R^6$, $R^7$, and $R^8$ are as defined earlier may be carried out under conventional conditions. The base is not critical. Any base normally employed for aldol condensation reaction may be employed, like, metal hydrides such as NaH, or KH; metal alkoxides such as NaOMe, $K^tBuO^-$, or NaOEt; metal amides such as $LiNH_2$, or $LiN(ipr)_2$. Aprotic solvent such as THF, ether, or dioxane may be used. The reaction may be carried out in an inert atmosphere which may be maintained by using inert gases such as $N_2$, Ar, or He and the reaction is more effective under anhydrous conditions. Temperature in the range of −80° C. to 25° C. may be used. The β-hydroxy aldol product may be dehydroxylated using conventional methods, conveniently by ionic hydrogenation technique such as by treating with a trialkyl silane in the presence of an acid such as trifluoroacetic acid. Solvent such as $C_2Cl_2$ may be used. Favorably, reaction proceeds at 25° C. Higher temperature may be employed if the reaction is slow.

Route (12): The reaction of a compound of general formula (IIIg) where all symbols are as defined earlier with a compound of general formula (If) where $L^1$ is a leaving group such as halogen atom, p-toluenesulfonate, methanesulfonate, trifluoromethanesulfonate and the like, preferably a halogen atom and all other symbols are as defined earlier to produce a compound of general formula (I) may be carried out in the presence of solvents such as DMSO, DMF, DME, THF, dioxane, ether and the like or a combination thereof. The reaction may be carried out in an inert atmosphere which may be maintained by using inert gases such as $N_2$, Ar, or He. The reaction may be effected in the presence of a base such as alkalis like sodium hydroxide, or potassium hydroxide; alkali metal carbonates like sodium carbonate, or potassium carbonate; alkali metal hydrides such as sodium hydride or potassium hydride; organometallic bases like n-butyl lithium, alkali metal amides like sodamide or mixtures thereof. The amount of base may range from 1 to 5 equivalents, based on the amount of the compound of formula (IIIg), preferably the amount of base ranges from 1 to 3 equivalents. The reaction may be carried out in the presence of phase transfer catalysts such as tetraalkylammonium halides or hydroxides. The reaction may be carried out at a temperature in the range of 0° C. to 150° C., preferably at a temperature in the range of 15° C. to 100° C. The duration of the reaction may range from 0.25 to 24 hours, preferably from 0.25 to 12 hours.

The compound of general formula (I) where Y represents oxygen and $R^8$ is as defined earlier may be converted to compound of formula (I), where Y represents $NR^{10}$ by reaction with appropriate amines. Suitably the compound of formula (I) where $YR^8$ represents OH may be converted to acid halide, preferably $YR^8$=Cl, by reacting with appropriate reagents such as oxalyl chloride, thionyl chloride and the like, followed by treatment with amines. Alternatively, mixed anhydrides may be prepared from compound of formula (I) where $YR^8$ represents OH and all other symbols are as defined earlier by treating with acid halides such acetyl chloride, acetyl bromide, pivaloyl chloride, dichlorobenzoyl chloride and the like. The reaction may be carried out in the presence of suitable base such as pyridine, triethylamine, diisopropyl ethyl amine and the like. Solvents such as halogenated hydrocarbons like $CHCl_3$, or $CH_2Cl_2$; hydrocarbons such as benzene, toluene, xylene and the like may be used. The reaction may be carried out at a temperature in the range of −40° C. to 40° C., preferably 0° C. to 20° C. The acid halide or mixed anhydride thus prepared may further be treated with appropriate amines.

The processes for the preparation of compounds of general formula (IIIa) have been described in a copending application Ser. No. 08/982,910.

In another embodiment of the present invention the novel intermediate of formula (If)

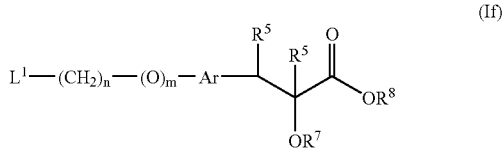
(If)

where Ar represents an optionally substituted divalent single or fused aromatic or heterocyclic group; $R^5$ represents hydrogen atom, hydroxy, alkoxy, halogen, lower alkyl, optionally substituted aralkyl group or forms a bond together with the adjacent group $R^6$; $R^6$ represents hydrogen, hydroxy, alkoxy, halogen, lower alkyl group, acyl, optionally substituted aralkyl or $R^6$ forms a bond together with $R^5$; $R^7$ represents hydrogen or optionally substituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl, or heteroaralkyl groups; $R^8$ may be hydrogen or optionally substituted groups selected from alkyl, cycloalkyl, aryl, aralkyl, heterocyclyl, heteroaryl, or heteroaralkyl groups; n is an integer ranging from 1–4; m is an integer 0 or 1 and $L^1$ is a leaving group such as halogen atom, p-toluenesulfonate, methanesulfonate, trifluoromethanesulfonate and the like, preferably a halogen atom and a process for its preparation and its use in the preparation of β-aryl-α-substituted hydroxyalkanoic acids is provided.

The compound of formula (If) where m=0 and all other symbols are as defined may be prepared by reacting a compound of formula (Ic)

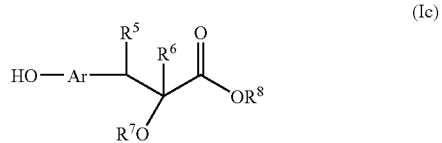
(Ic)

where $R^5$, $R^6$, $R^7$, $R^8$, and Ar are as defined earlier, with a compound of formula (IV)

$$L^1\text{-}(CH_2)_n\text{-}L^2 \quad (IV)$$

where $L^1$ and $L^2$ may be same or different and represent a leaving group such as Cl, Br, I, methanesulfonate, trifluoromethanesulfonate, p-toluenesulfonate and the like or $L^2$ may also represent a hydroxy or a protected hydroxy group which may be later converted to a leaving group; n represents an integer ranging from 1–4.

The reaction of compound of formula (Ic) with a compound of formula (IV) to produce a compound of formula (If) may be carried out in the presence of solvents such as THF, DMF, DMSO, DME and the like or mixtures thereof. The reaction may be carried out in an inert atmosphere, which may be maintained by using inert gases such as $N_2$, Ar or He. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from 20° C.–120° C., preferably at a temperature in the range of 30° C.–80° C. The duration of the reaction may range from 1 to 24 hours, preferably from 2 to 12 hours.

Alternatively, intermediate of formula (If) may be prepared by reacting a compound of formula (V)

$$L^1\text{-}(CH_2)_n\text{---}(O)_m\text{---}Ar\text{---}CHO \quad (V)$$

where where $L^1$ represent a leaving group such as Cl, Br, I, methanesulfonate, trifluoromethanesulfonate, p-toluenesulfonate and the like and all other symbols are as defined earlier, with a compound of formula (IIIb)

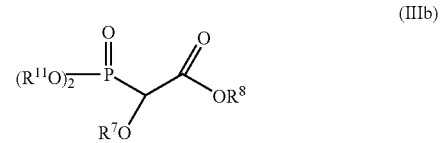
(IIIb)

where all symbols are as defined earlier, to yield a compound of formula (IIIf) which is further reduced to yield a compound of formula (If). The compound of formula (IIIf) represents a compound of formula (If) wherein $R^5$ and $R^6$ together represent a bond and all other symbols are as defined earlier.

The reaction of compound of formula (V) with (IIIb) may be carried out in the presence of a base such as alkali metal hydrides like NaH, or KH or organolithiums like $CH_3Li$, BuLi and the like or alkoxides such as NaOMe, NaOEt, $K^+BuO^-$ or mixtures thereof. The reaction may be carried out in presence of solvents such as THF, dioxane, DMF, DMSO, DME and the like or mixtures thereof. HMPA may be used as cosolvent. The reaction temperature may range from −78° C. to 50° C., preferably at a temperature in the range of −10° C. to 30° C. The reduction of compound of the formula (IIIf)

may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate, ethanol and the like. The nature of the solvent is not critical. A pressure between atmospheric pressure and 80 psi may be employed. Higher pressures may be used to reduce the reaction time. The catalyst may be preferably 5–10% Pd/C and the amount of catalyst used may range from 1–100% w/w. The reaction may also be carried out by employing metal solvent reduction such as magnesium in alcohol or sodium amalgam in alcohol.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) where $YR^8$ represents OH may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The present invention also provides a pharmaceutical composition, containing one or more compounds of the general formula (I), as defined above, their tautomeric forms, their stereoisomers, their polymorphs, their pharmaceutically acceptable salts, their pharmaceutically acceptable solvates in combination with the usual pharmaceutically employed carriers, diluents and the like, useful for the treatment and/or prophylaxis of insulin resistance (type 2 diabetes), impaired glucose tolerance, dyslipidemia, disorders related to syndrome X such as hypertension, obesity, insulin resistance, atherosclerosis, hyperlipidemia, coronary heart disease and other cardiovascular disorders. The compounds of the present invention are also useful for the treatment of certain renal diseases including glomerulonephritis, glomerulosclerosis, nephrotic syndrome, hypertensive nephrosclerosis, for the treatment of psoriasis, and polycystic ovarian syndrome (PCOS). These compounds may also be useful as aldose reductase inhibitors, for improving cognitive functions in dementia and treating diabetic complications and osteoporosis.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

Preparation 1

Ethyl (E/Z)-3-[4-benzyloxyphenyl]-2-ethoxypropanoate

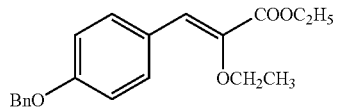

A solution of triethyl-2-ethoxyphosphonoacetate prepared by the method of Grell and Machleidt, *Annalen. Chemie,* 1996, 699, 53 (3.53 g, 13.2 mmol) in dry tetrahydrofuran (10 mL) was added slowly to a stirred ice cooled suspension of sodium hydride (60% dispersion of oil) (0.62 g, 25.94 mmol) in dry tetrahydrofuran (5 mL), under a nitrogen atmosphere. The mixture was stirred at 0° C. for 30 min. prior to the addition of a 4-benzyloxybenzaldehyde (2.5 g, 11.79 mmol) in dry tetrahydrofuran (20 mL). The mixture was allowed to warm up to room temperature and stirred at that temperature for further 20 h. The solvent was evaporated, water (100 mL) was added and extracted with ethyl acetate (2×75 ml). The combined organic extracts were washed with water (50 mL), brine (50 mL), dried ($Na_2SO_4$), filtered and the solvent was evaporated under reduced pressure. The residue was chromatographed over silica gel using a mixture of ethyl acetate and pet. ether (2:8) as an eluent to afford the title compound (3.84 g, quantitative) as an oil. $^1$H NMR of the product suggests a (76:24=Z:E) mixture of geometric isomers (R. A. Aitken and G. L. Thom, *Synthesis,* 1989, 958).

$^1$H NMR ($CDCl_3$, 200 MHz): δ 1.25–1.50 (complex, 6H), 3.85–4.03 (complex, 2H), 4.28 (q, J=7.0 Hz, 2H), 5.05, 5.09 (2s, 2H, benzyloxy $CH_2$), 6.08 (s, 0.24H, E isomer of olefinic proton), 6.85–6.90 (complex, 2H), 6.99 (s, 0.76H, Z isomer) 7.33–7.45 (complex, 5H), 7.75 (d, J=8.72 Hz, 2H).

Preparation 2

Methyl 3-[4-benzyloxyphenyl]-2-ethoxypropanoate

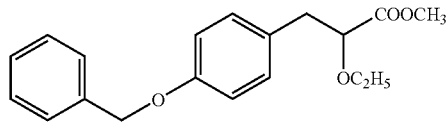

A mixture of ethyl (E/Z)-3-[4-benzyloxyphenyl]-2-ethoxypropanoate (3.84 g, 11.79 mmol obtained in the preparation 1) and magnesium turnings (5.09 g, 0.21 mol) in dry methanol (40 mL) was stirred at 25° C. for 1 h. Water (80 mL) was added and pH of the solution was adjusted to 6.5–7.5 with 2 N hydrochloric acid. The solution was extracted with ethyl acetate (3×75 mL). The organic layers were washed with water (50 mL), brine (50 mL) dried ($Na_2SO_4$) and filtered. The solvent was evaporated under reduced pressure to afford the title compound (3.7 g, quantitative yield) as an oil.

$^1$H NMR ($CDCl_3$, 200 MHz): δ 1.16 (t, J=6.97 Hz, 3H), 2.95 (d, J=6.55 Hz, 2H), 3.30–3.38 (complex, 1H), 3.55–3.67 (complex, 1H), 3.69 (s, 3H), 3.99 (t, J=6.64 Hz, 1H), 5.04 (s, 2H), 6.89 (d, J=8.63 Hz, 2H), 7.15 (d, J=8.62 Hz, 2H), 7.31–7.41 (complex, 5H).

Preparation 3

Methyl 3-(4-hydroxyphenyl)-2-ethoxypropanoate

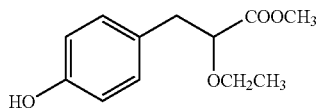

A suspension of methyl 3-[4-(benzyloxyphenyl)-2-ethoxypropanoate (3.7 g, 11.78 mmol; preparation 2) and 10% Pd—C (0.37 g) in ethyl acetate (50 mL) was stirred at 25° C. under 60 psi hydrogen pressure for 24 h. The catalyst was filtered and the solvent was evaporated under reduced pressure. The residue was chromatographed over silica gel using a mixture of ethyl acetate and pet. ether (2:8) as an eluent to afford the title compound (2.2 g, 84%) as an oil.

$^1$H NMR ($CDCl_3$, 200 MHz): δ 1.21 (t, J=6.97 Hz, 3H), 2.99 (d, J=6.37 Hz, 2H), 3.32–3.49 (complex, 1H), 3.57–3.65 (complex, 1H), 3.76 (s, 3H), 4.05 (t, J=6.64 Hz, 1H), 5.19–5.40 (bs, 1H, $D_2O$ exchangeable), 6.80 (d, J=8.44 Hz, 2H), 7.14 (d, J=8.39 Hz, 2H).

Preparation 4

Ethyl 3-[4-hydroxyphenyl]-2-ethoxypropanoate

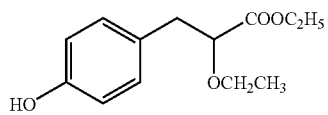

The title compound (1.73 g, 61%) was prepared as a colorless oil from ethyl (E/Z)-3-[4-benzyloxyphenyl]-2-ethoxypropenoate (3.85 g, 11.80 mmol) obtained in preparation 1 by hydrogenation procedure described in preparation 3.

$^1$H NMR ($CDCl_3$, 200 MHz): δ 1.12–1.29 (complex, 6H), 2.93 (d, J=6.55 Hz, 2H), 3.28–3.45 (complex, 1H), 3.51–3.68 (complex, 1H), 3.98 (t, J=6.55 Hz, 1H), 4.16 (q, J=7.15 Hz, 2H), 5.40 (s, 1H, $D_2O$ exchangeable), 6.73 (d, J=8.39 Hz, 2H), 7.08 (d, J=8.53 Hz, 2H).

Preparation 5

Ethyl 3-[4-benzyloxyphenyl]-2-butoxypropanoate

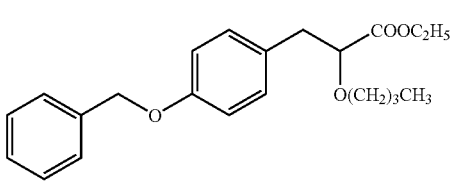

A solution of ethyl 3-[4-benzyloxyphenyl)-2-hydroxypropanoate (5.0 g, 16.6 mmol) (prepared in a similar manner as described in Ref: WO95/18125) in dry dimethyl formamide (5 mL) was aided to a suspension of sodium hydride (0.1 g, 41.6 mmol) (60% dispersion in oil) in dry dimethyl formamide (3 mL) at 0° C. and stirring was continued for further 1 h. To the above reaction mixture n-butyl bromide (3.4 g, 24.0 mmol) was added at 0° C. and stirring was continued for 10 h at ca. 25° C. Water (30 mL) was added and extracted with ethyl acetate (2×50 mL). The combined ethyl acetate layer was washed with water (50 mL), brine (25 mL), dried ($Na_2SO_4$), filtered and the solvent was evaporated. The residue was chromatographed over silica gel using a mixture of ethyl acetate and and pet. ether (1:9) as an eluent to afford the title compound (0.7 g, 20%) as an oil.

$^1$H NMR ($CDCl_3$, 200 MHz): δ 0.85 (t, J=7.38 Hz, 3H), 1.18–1.40 (complex, 5H), 1.49–1.58 (complex, 2H), 2.94 (d, J=6.74 Hz, 2H), 3.20–3.33 (complex, 1H), 3.46–3.61 (complex, 1H), 3.94 (t, J=6.37 Hz, 1H), 4.16 (q, J=7.0 Hz, 2H), 5.04 (s, 2H), 6.89 (d, J=8.5 Hz, 2H), 7.15 (d, J=8.48 Hz, 2H), 7.30–7.44 (complex, 5H).

Preparation 6

Ethyl 3-[4-hydroxyphenyl]-2-butoxypropanoate

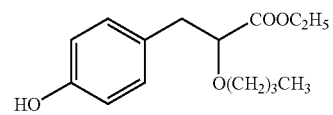

The title compound (0.475 g, 75%) was prepared as an oil from ethyl 3-[4-bezyloxyphenyl)-2-butoxypropanoate (0.85 g, 2.38 mmol) obtained in preparation 8 by an analogous procedure to that described in preparation 3.

$^1$H NMR ($CDCl_3$, 200 MHz): δ 0.85 (t, J=7.24 Hz, 3H), 1.19–1.38 (complex, 5H), 1.44–1.58 (complex, 2H), 2.94 (d, J=6.55 Hz, 2H), 3.21–3.32 (complex, 1H), 3.49–3.62 (complex, 1H), 3.94 (t, J=6.88 Hz, 1H), 4.16 (q, J=7.1 Hz, 2H), 4.99 (s, 1H, $D_2O$ exchangeable), 6.73 (d, J=8.53 Hz, 2H), 7.09 (d, J=8.44 Hz, 2H).

Preparation 7

Ethyl 3-[4-benzyloxyphenyl]-2-hexyloxypropanoate

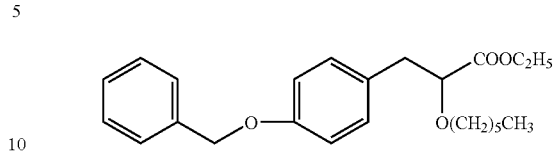

The title compound (1.2 g, 22%) was prepared as an oil from ethyl 3-(4-benzyloxyphenyl)-2-hydroxypropanoate (4.2 g, 14.0 mmol) and 1-bromohexane (3.4 g, 21.0 mmol) by an analogous procedure to that described in preparation 5.

$^1$H NMR ($CDCl_3$, 200 MHz): δ 0.86 (t, J=5.9 Hz, 3H), 1.18–1.37 (complex, 7H), 1.45–1.66 (complex, 4H), 2.94 (d, J=6.55 Hz, 2H), 3.22–3.33 (complex, 1H), 3.52–3.64 (complex, 1H), 3.94 (t, J=6.9 Hz, 1H), 4.16 (q, J=7.06 Hz, 2H), 5.03 (s, 2H), 6.89 (d, J=8.63 Hz, 2H), 7.15 (d, J=8.63 Hz, 2H), 7.31–7.44 (complex, 5H).

Preparation 8

Ethyl 3-[4-hydroxyphenyl]-2-hexyloxypropanoate

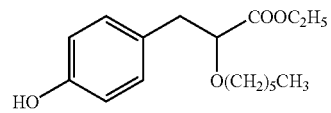

The title compound (0.7 g, 76%) was prepared as an oil from ethyl 3-[4-benzyloxyphenyl)-2-hexyloxypropanoate (1.2 g, 3.1 mmol) obtained in preparation 7 by an analogous procedure to that described in preparation 3.

$^1$H NMR ($CDCl_3$, 200 MHz): δ 0.85 (t, J=5.81 Hz, 3H), 1.19–1.39 (complex, 7H), 1.48–1.68 (complex, 4H), 2.92 (d, J=6.74 Hz, 2H), 3.18–3.39 (complex, 1H), 3.48–3.62 (complex, 1H), 3.93 (t, J=7.0 Hz, 1H), 4.16 (q, J=7.06 Hz, 2H), 4.85 (s, 1H, $D_2O$ exchangeable), 6.73 (d, J=8.53 Hz, 2H), 7.10 (d, J=8.31 Hz, 2H).

Preparation 9

Ethyl (E/Z)-3-[4-(2-bromoethoxy)phenyl]-2-ethoxypropenoate

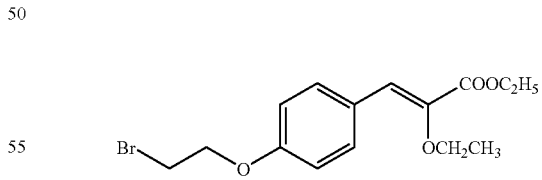

The title compound (4.0 g, 66%) was prepared as an oil in 45: 55 ratio of E:Z isomers (as measured by $^1$H NMR) from 4-(2-bromoethoxy)benzaldehyde (4.0 g, 17.4 mmol) and triethyl-2-ethoxyphosphonoacetate (5.61 g, 20.89 mmol) by an analogous procedure to that described in preparation 1.

$^1$H NMR ($CDCl_3$, 200 MHz): δ 1.17 and 1.42 (6H, E and Z triplets, isomeric —$OCH_2CH_3$ and $OCH_2$—$CH_3$), 3.62–3.72 (complex, 214), 3.90–4.28 (complex, 2H), 4.30–4.37 (complex, 4H), 6.09 (s, 0.45H, olefinic proton of E isomers), 6.85 and 6.92 (2H, d and d, J=8.67 Hz and 8.7 Hz), 6.98 (s, 0.55H, Z isomer of olefinic proton), 7.16 and 7.78 (d and d, combined 2H, J=8.63 Hz and 8.72 Hz).

Preparation 10

Ethyl 3-[4-(2-bromoethoxy)phenyl]-2-ethoxypropanoate

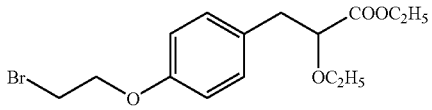

The title compound (4.0 g, 80%) was prepared as colorless oil from ethyl (E/Z)-3-[4-(2-bromoethoxy)phenyl]-2-ethoxypropenoate (5.0 g, 14.5 mmol) obtained in preparation 9 using $H_2$/10% Pd—C (4 g) in dioxane as a solvent by an analogous procedure to that described in preparation 3.

$^1$H NMR (CDCl$_3$, 200 MHz): δ 1.12–1.30 (complex, 6H), 2.95 (d, J=6.64 Hz, 2H), 3.25–3.45 (complex, 1H), 3.56–3.68 (complex, 3H), 3.96 (t, J=6.65 Hz, 1H), 4.16 (q, J=7.1 Hz, 2H), 4.27 (t, J=6.3 Hz, 2H), 6.81 (d, J=8.67 Hz, 2H), 7.16 (d, J=8.63 Hz, 2H).

EXAMPLE 1

Ethyl (E/Z)-3-[4-[2-(Phenothiazin-10-yl)ethoxy]phenyl]-2-ethoxypropenoate

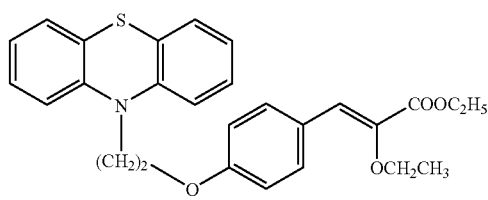

The title compound was obtained as 1:1 E:Z isomers (1.46 g, quantitative) as a syrupy liquid from 4-[2-(phenothiazin-10-yl)ethoxy]benzaldehyde (1.08 g, 3.11 mmol) and tri-ethyl-2-ethoxyphosphonoacetate (W. Grell & H. Machleidt, *Annalen chemie*, 1966, 699, 53) (1.0 g, 3.73 mmol) by an analogous procedure to that described in preparation 1.

$^1$H NMR (CDCl$_3$, 200 MHz): δ 1.15–1.43 (complex, 6H), 3.89–4.03 (complex, 2H), 4.11–4.17 (complex, 2H), 4.30, 4.33 (combined, 4H, —CH$_2$CH$_2$-singlets), 6.07 (s, 0.5H, olefinic proton of E isomer), 6.80–7.10 (complex, 6.5H), 7.14–7.20 (complex, 4H), 7.73 (d, J=8.39 Hz, 2H).

EXAMPLE 2

Ethyl (E/Z)-3-[4-[2-[phenothiazin-10-yl)methylbenzofuran-5-yl)-2-ethoxypropenoate

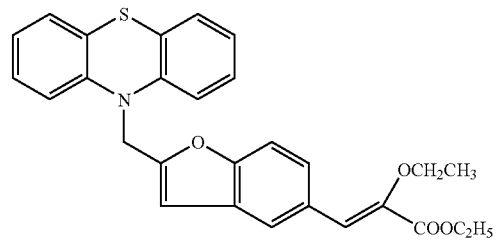

The title compound was obtained as E:Z isomers (38:62) (as measured by $^1$H NMR) (1.5 g, 100%) as a colorless liquid from 5-formyl-2-(phenothiazin-10-yl) methylbenzofuran (1.14 g, 3.2 mmol) by a procedure similar to that described for preparation 1.

$^1$HNMR (CDCl$_3$, 200 MHz): δ 1.23–1.45 (complex, 6H), 3.55–3.78 (complex, 1H), 3.88–4.19 (complex, 1H), 4.22–4.35 (complex, 2H), 5.14 (s, 2H), 6.18 (s, 0.38H, olefinic proton of E isomer) 6.47 and 6.54 (combined, 1H), 6.78–7.12 (complex, 8.62H), 7.37–7.48 (complex, 1H), 7.71 (d, J=7.57 Hz, 1H), 7.95 (s, 1H).

EXAMPLE 3

Ethyl (E/Z)-3-[4-[2-(phenoxazin-10-yl)ethoxy]phenyl]-2-ethoxypropenoate

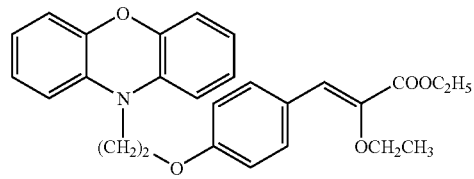

The title compound (14.4 g, 76%) was obtained as E:Z isomers (36:64) (as measured by $^1$H NMR) as a white solid from 4-[2-(phenoxazin-10-yl)ethoxy]benzaldehyde (14.0 g, 42.3 mmol) by an analogous procedure to that described for preparation 1. mp: 110–112° C.

$^1$H NMR (CDCl$_3$, 200 MHz): δ 1.16 and 1.38 (combined, 6H, isomeric —OCH$_2$CH$_3$ triplet signals), 3.89–4.05 (complex, 4H), 4.14–4.31 (complex, 4H), 6.06 (s, 0.36H, olefinic proton of E isomer), 6.66–6.95 (complex, 10.64H), 7.75 (d, J=8:76 Hz, 2H).

EXAMPLE 4

Methyl 3-[4-[2-(phenothiazin-10-yl)ethoxy]phenyl]-2-ethoxypropanoate

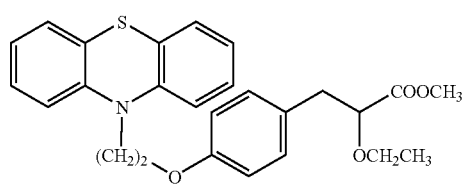

The title compound (1.3 g, 94%) was prepared as a gummy liquid from ethyl (E/Z)-3-[4-[2-(phenothiazin-10-yl)ethoxy]phenyl]-2-ethoxypropenoate (1.43 g, 3.10 mmol) obtained in example 1 by an analogous procedure to that described in preparation 2.

$^1$H NMR (CDCl$_3$, 200 MHz): δ 1.15 (t, J=7.0 Hz, 3H), 2.93 (d, J=6.64 Hz, 2H), 3.33–3.42 (complex, 1H), 3.52–3.63 (complex, 1H), 3.69 (s, 3H), 3.97 (t, J=6.2 Hz, 1H), 4.29 (s, 4H), 6.81 (d, J=8.62 Hz, 2H), 6.92–6.96 (complex, 4H), 7.12–7.22 (complex, 6H).

EXAMPLE 5

Methyl 3-[2-(phenothiazin-10-yl)methylbenzofuran-5-yl]-2-ethoxypropanoate

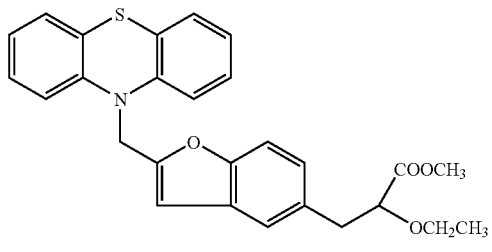

The title compound (1.0 g, 68%) was prepared as a gum, from ethyl (E/Z)-3-[2-(phenothiazin-10-yl)methylbenzofuran-5-yl]-2-ethoxypropenoate (1.5 g, 3.0 mmol) obtained in example 2 by an analogous procedure to that described in preparation 2.

$^1$H NMR (CDCl$_3$, 200 MHz): δ 1.16 (t, J=7.0 Hz, 3H), 3.07 (d, J=6.55 Hz, 2H), 3.30–3.49 (complex, 1H), 3.56–3.68 (complex, 1H), 3.70 (s, 3H), 4.05 (t, J=6.3 Hz, 1H), 5.13 (s, 2H), 6.48 (s, 1H), 6.79–7.48 (complex, 11H).

EXAMPLE 6

Methyl 3-[4-[2-(phenoxazin-10-yl)ethoxy]phenyl]-2-ethoxypropanoate

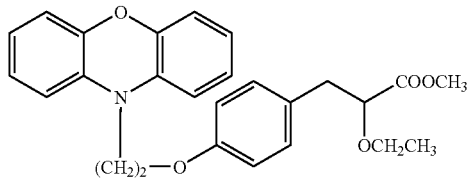

Method A

The title compound (0.68 g, 52%) was prepared as a white solid, from ethyl (E/Z)-3-[4-[2-(phenoxazin-10-yl)ethoxy]phenyl]-2-ethoxypropenoate (1.3 g, 2.9 mmol) obtained in example 3 by a procedure similar to that described in preparation 2, mp: 88–90° C.

Method B

A mixture of 2-(phenoxazin-10-yl)ethyl methanesulfonate (1.75 g, 5.0 mmol), methyl 3-(4-hydroxyphenyl)-2-ethoxypropanoate (1.5 g, 0.68 mmol) and potassium carbonate (3.16 g) in dry dimethylformamide (20 mL) was stirred for 12 h at 80° C. The reaction mixture was cooled to room temperature (ca. 25° C.). Water (30 mL) was added and extracted with ethyl acetate (2×50 mL). The combined organic extracts were washed with water (50 mL), dried (Na$_2$SO$_4$) and evaporated. The residue was chromatographed using a mixture of ethyl acetate and pet. ether (1:9) to afford the title compound (1.15 g, 47%) as a white solid. mp: 89–90° C. $^1$H NMR data matches with the desired product (see above).

$^1$H NMR (CDCl$_3$, 200 MHz): δ 1.16 (t, J=6.92 Hz, 3H), 2.96 (d, J=6.64 Hz, 2H), 3.22–3.40 (complex, 1H), 3.51–3.66, (complex, 1H), 3.68 (s, 3H), 4.00 (t, J=7.0 Hz, 1H), 4.18 (complex, 4H), 6.55–6.89 (complex, 10H), 7.12 (d, J=8.63 Hz, 2H).

EXAMPLE 7

Ethyl 3-[4-[2-(phenoxazin-10-yl)ethoxy]phenyl-2-ethoxypropanoate

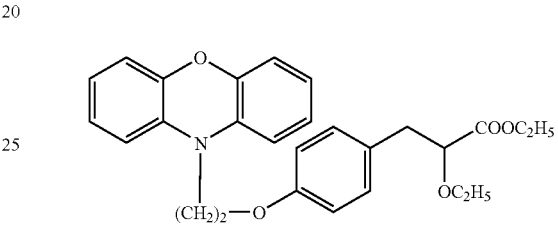

Method A

To a solution ethyl (E/Z)-3-[4-[2-(phenoxazin-10-yl)ethoxy]phenyl]-2-ethoxypropenoate (1.0 g, 2.24 mmol) obtained in example 3 in dioxane (50 mL) was added 10% Pd—C (0.25 g) and stirred at 25° C. under 60 psi hydrogen pressure for 24 h. At the end of this time reaction mixture was filtered and solvent was evaporated under reduced pressure. The residue was triturated with pet. ether to afford the title compound (0.96 g, 96%) as a white solid. mp: 51–53° C.

$^1$H NMR (CDCl$_3$, 200 MHz): δ 1.12–1.27 (complex, 6H), 2.94 (d, J=6.31 Hz, 2H), 3.26–3.41 (complex, 1H), 3.52–3.75 (complex, 1H), 3.96 (t, J=6.64 Hz, 2H), 4.10–4.28 (complex, 5H), 6.55–6.92 (complex, 10H), 7.16 (d, J=8.39 Hz, 2H).

Method B

The title compound (0.55 g, 75%) was prepared as a white solid from 2-(phenoxazin-10-yl)ethyl methanesulfonate (0.5 g, 1.63 mmol) and ethyl 3-(4-hydroxyphenyl)-2-ethoxypropanoate (0.46 g, 1.9 mmol) obtained in preparation 4 by a procedure similar to that described in example 6 (Method B). mp: 52–53° C. The $^1$H NMR data matches with the desired product (see above).

Method C

To a suspension of sodium hydride (60% dispersion in oil) (0.098 g, 4.0 mmol) in dry dimethyl formamide (3 mL) was added a solution of phenoxazine (0.3 g, 1.6 mmol) in dry dimethyl formamide (5 mL) at 0° C. under nitrogen atmosphere and stirring was continued for a further 30 min at ca. 25° C. To the above reaction mixture a solution of ethyl 3-[4-(2-bromoethoxy)phenyl]-2-ethoxypropanoate (0.85 g, 2.4 mmol) obtained in preparation 10 in dry dimethyl formamide (5 mL) at 0° C. and stirring was continued for a further 10 h at ca. 25° C. Water (40 mL) was added and extracted with ethyl acetate (2×30 mL). The combined organic extracts were washed with water (25 mL), brine (25 mL), dried (Na$_2$SO$_4$), filtered and evaporated. The residue was chromatographed over silica gel using a mixture of ethyl acetate and pet. ether (1:9) as an eluent to afford the title compound (0.3 g, 40%) as a colorless solid. mp: 52–53° C. The $^1$H NMR data matches with the desired product (see above).

EXAMPLE 8

Ethyl 3-[4-[2-(phenoxazin-10-yl)ethoxy]phenyl]-2-hydroxypropanoate

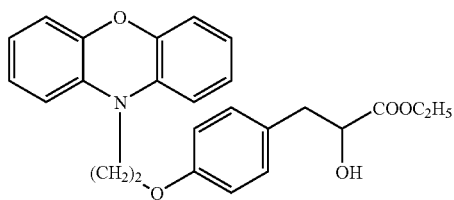

The title compound (1.06 g, 43%) as a pale yellow liquid from 2-(phenoxazin-10-yl)ethyl methanesulfonate (1.8 g, 5.9 mmol) and ethyl 2-hydroxy-3-(4-hydroxyphenyl)propanoate (1.36 g, 6.49 mmol) obtained in preparation 6 by an analogous procedure to that described in example 6 (Method B).

$^1$H NMR (CDCl$_3$, 200 MHz): δ 1.29 (t, J=6.96 Hz, 3H), 2.85–3.12 (complex, 2H), 3.92 (bs, 2H), 4.10–4.27 (complex, 4H), 4.39 (t, J=6.1 Hz, 1H), 6.68–6.89 (complex, 10H), 7.13 (d, J=8.39 Hz, 2H). OH proton is too broad to observe.

EXAMPLE 9

Ethyl 3-[4-[2-(phenoxazin-10-yl)ethoxy]phenyl]-2-butoxypropanoate

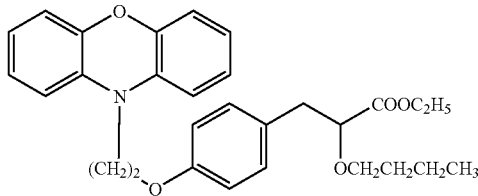

The title compound (0.25 g, 53%) was prepared as a colorless liquid from 2-(phenoxazin-10-yl)ethyl methanesulfonate (0.3 g, 0.98 mmol) and ethyl 2-butoxy-3-(4-hydroxyphenyl)propanoate (0.26 g, 0.97 mmol) obtained in preparation 6 by an analogous procedure to that described in example 6 (Method B).

$^1$H NMR (CDCl$_3$, 200 MHz): δ 0.92 (t, J=6.4 Hz, 3H), 1.21–1.39 (complex, 5H), 1.45–1.58 (complex, 2H), 2.94 (d, J=6.32 Hz, 2H), 3.24–3.31 (complex, 1H), 3.50–3.57 (complex, 11H), 3.94 (t, J=6.13 Hz, 1H), 4.13–4.23 (complex, 6H), 6.61–6.84 (complex, 10H), 7.16 (d, J=8.3 Hz, 2H).

EXAMPLE 10

Ethyl 3-[4-[2-(phenoxazin-10-yl)ethoxy]phenyl]-2-hexyloxypropanoate

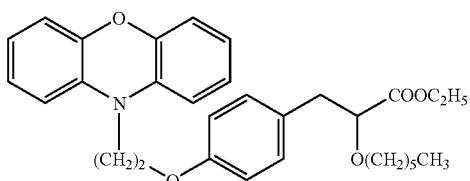

The title compound (0.52 g, 53%) was prepared as a pale yellow oil from 2-(phenoxazin-10-yl)ethyl methanesulfonate (0.6 g and 1.97 mmol) and ethyl 3-(4-hydroxyphenyl)-2-hexyloxypropanoate (0.70 g, 2.4 mmol) obtained in preparation 8 by an analogous procedure to that described in example 6 (Method B).

$^1$H NMR (CDCl$_3$, 200 MHz): δ 0.85 (t, J=6.0 Hz, 3H), 1.20–1.27 (complex, 7H), 1.48–1.57 (complex, 4H), 2.94 (d, J=6.0 Hz, 2H), 3.21–3.30 (complex, 1H), 3.52–3.56 (complex, 1H), 3.90–3.99 (complex, 3H), 4.13–4.22 (complex, 4H), 6.60–6.83 (complex, 10H), 7.15 (d, J=8.62 Hz, 2H).

EXAMPLE 11

3-[4-[2-(Phenothiazin-10-yl)ethoxy]phenyl]-2-ethoxypropanoic acid

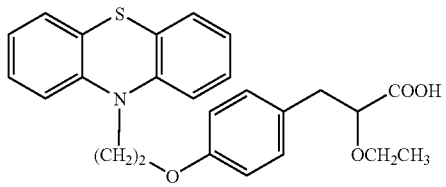

To a solution of methyl 3-[4-[2-(phenothiazin-10-yl)ethoxy]phenyl]-2-ethoxypropanoate (7.5 g, 16.70 mmol) obtained in example 4 in methanol (50 mL) was added aqueous 10% sodium hydroxide (20 mL). The reaction mixture was stirred at ca. 25° C. for 3 h. The solvent was removed under reduced pressure and the residue was acidified with 2 N hydrochloric acid, extracted with ethyl acetate (2×100 mL). The combined ethyl acetate extract was washed with water (50 mL), brine (50 mL), dried (Na$_2$SO$_4$), filtered and solvent was evaporated under reduced pressure. The residue was chromatographed over silica gel using a mixture of dichloromethane and methanol (9:1) as an eluent to afford the title compound (6.0 g, 83%) as a white solid. mp: 79–82° C.

$^1$H NMR (CDCl$_3$, 200 MHz): δ 1.18 (t, J=6.8 Hz, 3H), 2.88–3.11 (complex, 2H), 3.39–3.64 (complex, 2H), 4.06 (dd, J=9.2 and 4.3 Hz, 1H), 4.30 (s, 4H), 5.30–5.98 (bs, 1H, D$_2$O exchangeable), 6.80–7.02 (complex, 6H), 7.12–7.21 (complex, 6H).

EXAMPLE 12

3-[4-[2-(Phenothiazin-10-yl)ethoxy]phenyl]-2-ethoxypropanoic acid, sodium salt

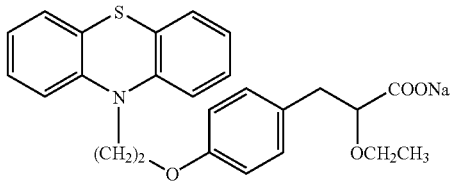

A mixture of 3-[4-[-2-(phenothiazin-10-yl)ethoxy]phenyl]-2-ethoxypropanoic acid (0.3 g, 0.689 mmol) sodium methoxide (0.041 g, 0.758 mmol) in methanol (5 mL) was stirred at ca. 25° C. for 2 h. The solvent was removed under reduced pressure and the residue was triturated with dry ether (3×10 mL). The separated solid was filtered, washed with dry ether (2×5 mL) and dried over $P_2O_5$ under reduced pressure to afford the title compound (0.25 g, 89%) as a white solid. mp: 188–191° C.

$^1$HNMR (DMSO-$d_6$, 200 MHz): δ 1.04 (t, J=6.9 Hz, 3H), 2.71–2.89 (complex, 1H), 2.90–3.06 (complex, 1H), 3.16–3.30 (complex, 1H), 3.36–3.54 (complex, 1H). 3.88–3.91 (complex, 1H), 4.21 (s, 4H), 6.72 (d, J=8.3 Hz, 2H), 6.89–6.99 (complex, 4H), 7.05–7.21 (complex, 6H).

EXAMPLE 13

3-[2-(Phenothiazin-10-yl)methylbenzofuran-5-yl]-2-ethoxypropanoic acid

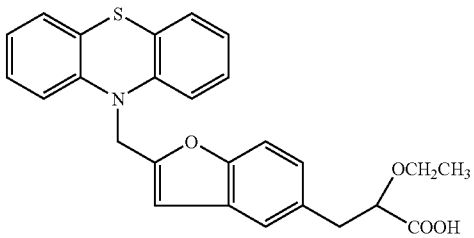

The title compound (0.8 g, 83%) was prepared as a white solid from methyl 3-[2-(phenothiazin-10-yl)methylbenzofuran-5-yl]-2-ethoxypropanoate (1.0 g, 2.0 mmol) obtained in example 5 by a procedure analogous to that described in example 10. mp: 120–121° C. COOH proton is too broad to observe.

$^1$H NMR (CDCl$_3$, 200 MHz): δ 1.15 (t, J=6.95 Hz, 3H), 3.00–3.26 (complex, 2H), 3.40–3.68 (complex, 2H), 4.08 (t, J=4.47 Hz, 1H), 5.11 (s, 2H), 6.46 (s, 1H), 6.77–7.40 (complex, 1H).

EXAMPLE 14

3-[2-(Phenothiazin-10-yl)methylbenzofuran-5-yl]-2-ethoxypropanoic acid, sodium salt

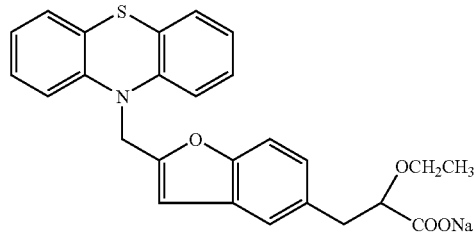

The title compound (0.12 g, 67%) was prepared as a white solid from 3-[2-[(phenothiazin-10-yl)methylbenzofuran-5-yl)-2-ethoxypropanoic acid (0.16 g, 0.38 mmol) obtained in example 13 by a procedure analogous to that described for example 12. mp: 258–261° C.

$^1$H NMR (CDCl$_3$, 200 MHz) δ: 0.95 (t, J=6.97 Hz, 3H), 2.62–2.80 (complex, 1H), 2.89–3.02 (complex, 1H), 3.06–3.18 (complex, 1H), 3.22–3.31 (complex, 1H) 3.50–3.61 (complex, 1H), 5.25 (s, 2H), 6.64 (s, 1H), 6.90–7.39 (complex, 11H).

EXAMPLE 15

3-[4-[2-(Phenoxazin-10-yl)ethoxy]phenyl]-2-ethoxypropanoic acid

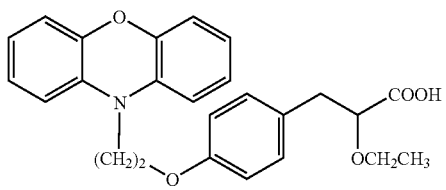

The title compound (5.4 g, 77%) was prepared as a white solid from methyl 3-[4-[2-(phenoxazin-10-yl)ethoxy]phenyl]-2-ethoxypropanoate (7.5 g, 16.8 mmol) obtained in example 6 by a procedure similar to that described in example 11. mp 90–92° C.

$^1$H NMR (CDCl$_3$, 200 MHz): δ 1.19 (t, J=7.0 Hz, 3H), 2.90–3.18 (complex, 2H), 3.41–3.62 (complex, 2H), 3.90–4.10 (complex, 3H), 4.18 (t, J=6.2 Hz, 2H), 6.58–6.89 (complex, 10H), 7.16 (d, J=8.4 Hz, 2H). COOH proton is too broad to observe.

EXAMPLE 16

3-[4-[2-(Phenoxazin-10-yl)ethoxy]phenyl]-2-ethoxypropanoic acid, sodium salt

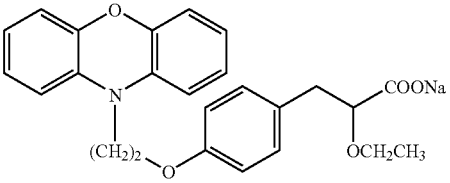

The title compound (0.27 g, 85%) was prepared as a white solid from 3-[4-[2-(phenoxazin-10-yl)ethoxy]phenyl-2- ethoxypropanoic acid (0.3 g, 0.72 mmol) obtained in example 15 by an analogous procedure to that described in example 12. mp: 194–202° C.

$^1$H NMR (CDCl$_3$, 200 Mhz): δ 0.92 (t, J=6.97 Hz, 3H), 2.65–2.82 (complex, 1H), 2.96–3.14 (complex, 2H), 3.31–3.41 (complex, 1H), 3.70–3.90 (complex, 3H), 3.94–4.04 (complex, 2H), 6.47–6.74 (complex, 10H), 7.05 (d, J=8.3 Hz, 2H).

EXAMPLE 17

3-[4-[2-(Phenoxazin-10-yl)ethoxy]phenyl]-2-hydroxypropanoic acid

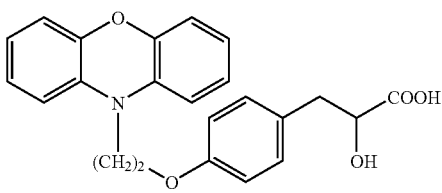

The title compound (0.40 g, 72%) was prepared as a brown liquid from 3-[4-[2-(phenoxazin-10-yl)ethoxy]phenyl]-2-hydroxypropanoate (0.6 g, 1.43 mmol) obtained in example 8 by an analogous procedure to that described in example 11.

$^1$H NMR (CDCl$_3$, 200 MHz) δ: 2.75 (bs, 1H, D$_2$O exchangeable), 2.86–3.23 (complex, 2H), 3.85 (t, J=6.0 Hz, 2H), 4.18 (t, J=5.9 Hz, 2H), 4.47 (complex, 1H), 6.58–6.89 (complex, 10H), 7.17 (d, J=8.63 Hz, 2H). COOH proton is too broad to observe.

EXAMPLE 18

3-[4-[2-(Phenoxazin-10-yl)ethoxy]phenyl]-2-butoxypropanoic acid

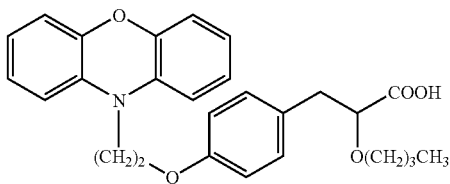

The title compound (0.13 g, 69%) was prepared as a cream colored solid from ethyl 3[-4-[2-(phenoxazin-10-yl)ethoxy]phenyl]-2-butoxypropanoate (0.2 g, 0.42 mmol) obtained in example 9 by an analogous procedure to that described in example 11. mp: 84–88° C.

$^1$H NMR (CDCl$_3$, 200 MHz): δ 0.88 (t, J=7.5 Hz, 3H), 1.26–1.47 (complex, 2H), 1.47–1.66 (complex, 2H), 2.87–3.16 (complex, 2H), 3.35–3.58 (complex, 2H), 3.88–4.08 (complex, 3H), 4.15 (t, J=6.4 Hz, 2H), 6.65–6.86 (complex, 10H), 7.15 (d, J=8.63 Hz, 2H). COOH proton is too broad to observe.

EXAMPLE 19

3-[4-[2-(Phenoxazin-10-yl)ethoxy]phenyl]-2-butoxypropanoic acid, sodium salt

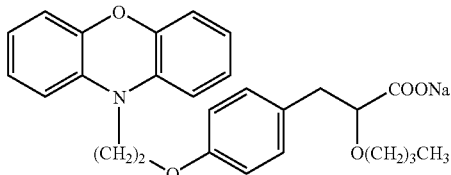

The title compound (0.07 g, 83%) was prepared as a cream colored hygroscopic solid from 3-[4-[2-(phenoxazin-10-yl)ethoxy]phenyl]-2-butoxypropanoic acid (0.08 g, 0.178 mmol) obtained in example 18 by a procedure similar to that described in example 12.

$^1$H NMR (DMSO-d$_6$, 200 MHz): δ 0.78 (t, J=7.28 Hz, 3H), 1.19–1.52 (complex, 4H), 2.72–3.02 (complex, 2H), 3.45–3.67 (complex, 2H), 4.01 (bs, 3H), 4.18 (bs, 2H), 6.61–6.89 (complex, 8H), 7.10–7.24 (complex, 4H).

EXAMPLE 20

3-[4-[2-(Phenoxazin-10-yl)ethoxy]phenyl]-2-hexyloxypropanoic acid

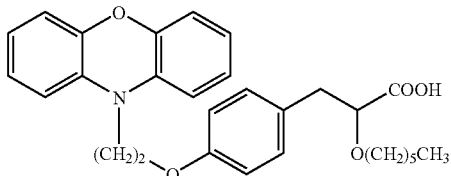

The title compound (0.10 g, 23%) was obtained as a syrupy liquid from ethyl 3-[4-[2-(phenoxazin-10-yl)ethoxy]phenyl]-2-hexyloxypropanoate (0.46 g, 0.96 mmol) obtained in example 10 by an analogous procedure to that described in example 11.

$^1$HNMR(CDCl$_3$, 200 MHz): δ 0.86 (t, J=6.0 Hz, 3H), 1.18–1.30 (complex, 4H), 1.42–1.80 (complex, 4H), 2.88–3.18 (complex, 2H), 3.32–3.60 (complex, 2H), 3.89–4.09 (complex, 3H), 4.16 (t, J=6.0 Hz, 2H), 6.58–6.89 (complex, 10H), 7.14 (d, J=8.63 Hz, 2H). COOH is too broad to observe.

EXAMPLE 21

[(2R)-N(1S)]-3-[4-[2-(Phenoxazin-10-yl)ethoxy]phenyl]-2-ethoxy-N-(2-hydroxy-1-phenylethyl)propanamide (21a)

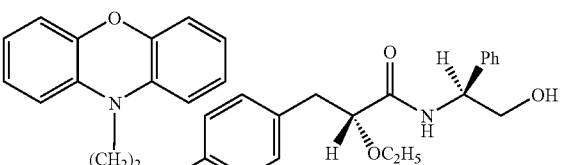

[(2S)-N(1S)]-3-[4-[2-(phenoxazin-10-yl)ethoxy]phenyl]-2-ethoxy-N-(2-hydroxy-1-phenylethyl)propanamide (21b)

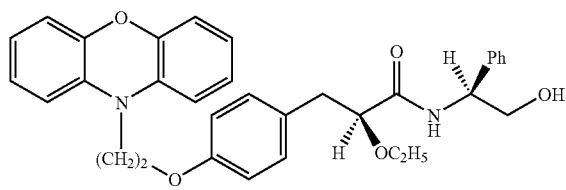

To an ice cooled solution of 3-[4-[2-(phenoxazin-10-yl)ethoxy]phenyl]-2-ethoxy propanoic acid (1.2 g, 2.9 mmol) obtained in example 15 and triethylamine (0.48 g, 5.8 mmol) in dry dichloromethane (25 mL) was added pivaloyl chloride (0.38 g, 3.19 mmol) and stirring was continued for further 30 min at 0° C. A mixture of (S)-2-phenylglycinol (0.39 g, 2.9 mmol) and triethylamine (0.58 g, 5.8 mmol) in dichloromethane (20 mL) was added to the above reaction mixture at 0° C. and stirring was continued for 2 h at 25° C. Water (50 mL) was added and extracted with dichloromethane (2×50 mL). The organic extracts were washed with water (2×25 mL) and brine (25 mL), dried ($Na_2SO_4$) and evaporated. The residue was chromatographed over silica gel using a gradient of 40–60% ethyl acetate in pet. ether as an eluent to afford firstly a diastereomer tentatively assigned as [2R, N(1S)]-3-[4-[2-(phenoxazin-10-yl)ethoxy]phenyl]-2-ethoxy-N-(2-hydroxy-1-phenylethyl)propanamide (0.55 g, 35%) (21 a) followed by of [2-N(1S)]-3-[4-[2-(phenoxazin-10-yl)ethoxy]phenyl]-2-ethoxy-N-(2-hydroxy-1-phenylethyl) propanamide (0.5 g, 32%) (21b).

21a: mp: 126–128° C.
$[\alpha]_D^{25}$=+24.6 (c=1.0%, $CHCl_3$).
$^1$H NMR ($CDCl_3$, 200 MHz): δ 1.16 (t, J=7.20 Hz, 3H), 2.50 (bs, 1H, $D_2O$ exchangeable), 2.92–3.20 (complex, 2H), 3.52 (q, J=7.05 Hz, 2H), 3.72 (bs, 2H), 3.99 (complex, 3H), 4.21 (t, J=6.64 Hz, 2H), 4.98–5.01 (complex, 1H), 6.64–6.70 (complex, 5H), 6.73–6.89 (complex, 4H), 7.03 (d, J=7.15 Hz, 1H), 7.18–7.29 (complex, 4H), (J=7.32–7.39 complex, 3H). CONH is too broad to observe.

21b: mp: 139–141° C.
$[\alpha]_D^{25}$=13.3 (c, 1.00%, $CHCl_3$)
$^1$H NMR ($CDCl_3$, 200 MHz): δ 1.18 (t, J=6.96 Hz, 3H), 2.05 (bs, 1H, D2O exchangeable), 2.80–3.14 (complex, 2H), 3.54 (q, J=7.0 Hz, 2H), 3.85 (bs, 2H), 3.97 (complex, 3H), 4.14 (t, J=6.23 Hz, 2H), 4.92–5.01 (complex, 1H), 6.62–6.85 (complex, 9H), 7.02–7.20 (complex, 5H), 7.26–7.30 (complex, 3H). CONH is too broad to observe.

EXAMPLE 22

(R)-3-[4-[2-(Phenoxazin-10-yl)ethoxy]phenyl]-2-ethoxypropanoic acid

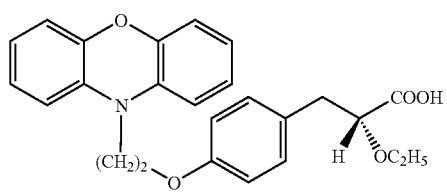

A solution of [2R diastereomer, N(1S)]-3-[4-[2-(phenoxazin-10-yl)ethoxy]phenyl]-2-ethoxy-N-(2-hydroxy-1-phenylethyl)propanamide (0.45 g, 0.84 mmol) obtained in example 21a in mixture of 1M sulphuric acid (17 mL) and dioxane/water (1:1, 39 mL) was heated in an oil bath at 100° C. for 60–68 h. The pH of the mixture was adjusted to 3.0 by addition of an aqueous sodium hydrogen carbonate solution. The mixture was extracted with ethyl acetate (2×25 mL) and the organic extract was washed with water (50 mL), brine (25 mL), dried ($Na_2SO_4$) and evaporated. The residue was chromatographed over silica gel using a gradient of 50–75% ethyl acetate in pet. ether to afford the title compound (0.2 g, 57%) as a white solid. mp: 77–78° C.

$[\alpha]_D^{25}$=+12.1 (c=1.0%, $CHCl_3$)
$^1$H NMR ($CDCl_3$, 200 MHz): δ 1.16 (t, J=7.0 Hz, 3H), 1.43–1.85 (bs, 1H, $D_2O$ exchangeable), 2.86–3.14 (complex, 2H), 3.40–3.67 (complex, 2H), 3.90–4.08 (complex, 3H), 4.15 (t, J=6.65 Hz, 2H), 6.59–6.83 (complex, 10H), 7.13 (d, J=8.4 Hz, 2H).

EXAMPLE 23

(S)-3-[4-[2-(phenoxazin-10-yl)ethoxy]phenyl]-2-ethoxypropanoic acid

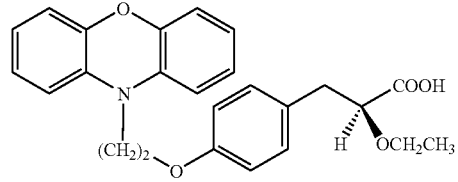

The title compound (0.19 g, 54%) was prepared as a white solid from diastereomer [(2S-N(1S)]-3-[4-[2-(phenoxazin-10-yl)ethoxy]phenyl]-2-ethoxy-N-(2-hydroxy-1-phenyl)propanamide (0.45 g, 0.84 mmol) obtained in example 21b by an analogous procedure to that described in example 22. mp 89–90° C.

$[\alpha]_D^{25}$=−12.6 (c=1.0%, $CHCl_3$)
$^1$H NMR ($CDCl_3$, 200 MHz): δ 1.16 (t, J=7.02 Hz, 3H), 1.42–1.91 (bs, 1H, $D_2O$ exchangeable), 2.94–3.15 (complex, 2H), 3.40–3.65 (complex, 2H), 3.86–4.06 (complex, 3H), 4.15 (t, J=6.65 Hz, 2H), 6.63–6.83 (complex, 10H), 7.13 (d, J=8.54 Hz, 2H).

The compounds of the present invention lowered random blood sugar level, triglyceride, total cholesterol, LDL, VLDL and increased HDL. This was demonstrated by in vitro as well as in vivo animal experiments.

Demonstration of Efficacy of Compounds:

A) In Vitro a) Determination of hPPARα Activity:

Ligand binding domain of hPPARα was fused to DNA binding domain of Yeast transcription factor GAL4 in eucaryotic expression vector. Using superfect (Qiagen, Germany) as transfecting reagent HEK-293 cells were transfected with this plasmid and a reporter plasmid harboring the luciferase gene driven by a GAL4 specific promoter. Compound was added at different concentrations after 42 hrs of transfection and incubated overnight. Luciferase activity as a function of compound binding/activation capacity of PPARα was measured using Packard Luclite kit (Packard, USA) in Top Count (Ivan Sadowski, Brendan Bell, Peter Broag and Melvyn Hollis. Gene. 1992. 118: 137–141; Superfect Transfection Reagent Handbook. February, 1997. Qiagen, Germany).

b) Determination of hPPARγ Activity:

Ligand binding domain of hPPARα was fused to DNA binding domain of Yeast transcription factor GAL4 in eucaryotic expression vector. Using lipofectamine (Gibco BRL, USA) as transfecting reagent HEK-293 cells were transfected with this plasmid and a reporter plasmid harboring the luciferase gene driven by a GAL4 specific promoter. Compound was added at 1 µM concentration after 48 hrs of transfection and incubated overnight. Luciferase activity as a function of drug binding/activation capacity of PPARγ1 was measured using Packard Luclite kit (Packard, USA) in Packard Top Count (Ivan Sadowski, Brendan Bell, Peter Broag and Melvyn Hollis. Gene. 1992. 118: 137–141; Guide to Eukaryotic Transfections with Cationic Lipid Reagents. Life Technologies, GIBCO BRL, USA).

| Example No | Concentration | PPARα | Concentration | PPARγ |
|---|---|---|---|---|
| Example 11 | 50 µM | 6.42 Fold | 1 µM | 5.20 Fold |
| Example 15 | 50 µM | 3.30 Fold | 1 µM | 6.0 Fold | c) Determination of HMG CoA Reductase Inhibition Activity: Liver microsome bound reductase was prepared from 2% cholestyramine fed rats at mid-dark cycle. Spectrophotometric assays were carried out in 100 mM $KH_2PO_4$, 4 mM DTT, 0.2 mM NADPH, 0.3 mM HMG CoA and 125 µg of liver microsomal enzyme. Total reaction mixture volume was kept as 1 ml. Reaction was started by addition of HMG CoA. Reaction mixture was incubated at 37° C. for 30 min and decrease in absorbance at 340 nm was recorded. Reaction mixture without substrate was used as blank (Goldstein, J. L and Brown, M. S. Progress in understanding the LDL receptor and HMG CoA reductase, two membrane proteins that regulate the plasma cholesterol. J. Lipid Res. 1984, 25: 1450–1461). The test compounds inhibited the HMG CoA reductase enzyme.

B) In Vivo:

a) Efficacy in Genetic Models:

Mutation in colonies of laboratory animals and different sensitivities to dietary regimens have made the development of animal models with non-insulin dependent diabetes and hyperlipidemia associated with obesity and insulin resistance possible. Genetic models such as db/db and ob/ob (Diabetes, (1982) 31(1): 1–6) mice and zucker fa/fa rats have been developed by the various laboratories for understanding the pathophysiology of disease and testing the efficacy of new antidiabetic compounds (Diabetes, (1983) 32: 830–838 Annu. Rep. Sankyo Res. Lab. (1994). 46: 1–57). The homozygous animals, C57 BL/KsJ-db/db mice developed by Jackson Laboratory, US. are obese, hyperglycemic, hyperinsulinemic and insulin resistant (J. Clin. Invest. (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, were used in the experiment. The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended on 0.25% carboxymethyl cellulose and administered to test group at a dose of 0.1 mg to 30 mg/kg through oral gavage daily for 6 days. The control group received vehicle (dose 10 ml/kg). On 6th day the blood samples were collected one hour after administration of test compounds/vehicle for assessing the biological activity.

The random blood sugar and triglyceride levels were measured by collecting blood (100 µl) through orbital sinus, using heparinised capillary in tubes containing EDTA which was centrifuged to obtain plasma. The plasma glucose and triglyceride levels were measured spectrometrically, by glucose oxidase and glycerol-3-$PO_4$ oxidase/peroxidase enzyme (Dr. Reddy's Lab. Diagnostic Division Kits, Hyderabad, India) methods respectively.

The blood sugar and triglycerides lowering activities of the test compound was calculated according to the formula.

No adverse effects were observed for any of the mentioned compounds of invention in the above test.

| Compound | Dose (mg/kg) | Reduction in Blood Glucose Level (%) | Triglyceride Lowering (%) |
|---|---|---|---|
| Example 14 | 3 | 52 | 61 |
| Example 11 | 10 | 66 | 50 |

The ob/ob mice were obtained at 5 weeks of age from Bomholtgard, Demark and were used at 8 weeks of age. Zucker fa/fa fatty rats were obtained from IffaCredo, France at 10 weeks of age and were used at 13 weeks of age. The animals were maintained under 12 hour light and dark cycle at 25±1° C. Animals were given standard laboratory chow (NIN, Hyderabad, India) and water, ad libitum (Fujiwara, T., Yoshioka, S., Yoshioka, T., Ushiyama, I and Horikoshi, H. Characterization of new oral antidiabetic agent CS-045. Studies in KK and ob/ob mice and Zucker fatty rats. Diabetes. 1988. 37: 1549–1558).

The test compounds were administered at 0.1 to 30 mg/kg/day dose for 9 days. The control animals received the vehicle (0.25% carboxymethylcellulose, dose 10 ml/kg) through oral gavage.

The blood samples were collected in fed state 1 hour after drug administration on 0 and 9 day of treatment. The blood was collected from the retro-orbital sinus through heparinised capillary in EDTA containing tubes. After centrifugation, plasma sample was separated for triglyceride, glucose, free fatty acid, total cholesterol and insulin estimations. Measurement of plasma triglyceride, glucose, total cholesterol were done using commercial kits (Dr. Reddy's Laboratory, Diagnostic Division, India). The plasma free fatty acid was measured using a commercial kit form Boehringer Mannheim, Germany. The plasma insulin was measured using a RIA kit (BARC, India). The reduction of various parameters examined are calculated according to the formula.

In ob/ob mice oral glucose tolerance test was performed after 9 days treatment. Mice were fasted for 5 hrs and challenged with 3 gm/kg of glucose orally. The blood samples were collected at 0, 15, 30, 60 and 120 min for estimation of plasma glucose levels.

The experimental results from the db/db mice, ob/ob mice, Zucker fa/fa rats suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

Blood glucose level and triglycerides are also lowered at doses greater than 10 mg/kg. Normally, the quantum of reduction is dose dependent and plateaus at certain dose.

b) Cholesterol Lowering, Activity in Hypercholesterolemic Rat Models

Male Sprague Dawley rats (NIN stock) were bred in DRF animal house. Animals were maintained under 12 hour light and dark cycle at 25±1° C. Rats of 180–200 gram body weight range were used for the experiment. Animals were made hypercholesterolemic by feeding 2% cholesterol and 1% sodium cholate mixed with standard laboratory chow [National Institute of Nutrition (NIN), Hyderabad, India] for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988. 74: 215–225).

The test compounds were administered orally at a dose 0.1 to 30 mg/kg/day for 3 days. Control group was treated with vehicle alone (0.25% Carboxymethylcellulose; dose 10 ml/kg).

The blood samples were collected in fed state 1 hour after drug administration on 0 and 3 day of compound treatment. The blood was collected from the retro-orbital sinus through heparinised capillary in EDTA containing tubes. After centrifugation, plasma sample was separated for total cholesterol, HDL and triglyceride estimations. Measurement of plasma triglyceride, total cholesterol and HDL were done using commercial kits (Dr. Reddy's Laboratory, Diagnostic Division, India). LDL and VLDL cholesterol were calculated from the data obtained for total cholesterol, HDL and triglyceride. The reduction of various parameters examined are calculated according to the formula.

c) Plasma Triglyceride and Total Cholesterol Lowering Activity in Swiss Albino Mice and Guinea Pigs:

Male Swiss albino mice (SAM) and male Guinea pigs were obtained from NIN and housed in DRF animal house. All these animals were maintained under 12 hour light and dark cycle at 25±1° C. Animals were given standard laboratory chow (NIN, Hyderabad, India) and water, ad libitum. SAM of 20–25 g body weight range and Guinea pigs of 500–700 g body weight range were used (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107–114).

The test compounds were administered orally to Swiss albino mice at 0.3 to 30 mg/kg/day dose for 6 days. Control mice were treated with vehicle (0.25% Carboxymethylcellulose; dose 10 ml/kg). The test compounds were administered orally to Guinea pigs at 0.3 to 30 mg/kg/day dose for 6 days. Control animals were treated with vehicle (0.25% Carboxymethylcellulose; dose 5 ml/kg).

The blood samples were collected in fed state 1 hour after drug administration on 0 and 6 day of treatment. The blood was collected from the retro-orbital sinus through heparinised capillary in EDTA containing tubes. After centrifugation, plasma sample was separated for triglyceride and total cholesterol (Wieland, O. Methods of Enzymatic analysis. Bergermeyer, H. O., Ed., 1963. 211–214; Trinder, P. Ann. Clin. Biochem. 1969. 6: 24–27). Measurement of plasma triglyceride, total cholesterol and HDL were done using commercial kits (Dr. Reddy's Diagnostic Division, Hyderabad, India).

Formulae for Calculation:

1. Percent reduction in Blood sugar/triglycerides/total cholesterol were calculated according to the formula:

$$\text{Percent reduction (\%)} = 1 - \frac{TT/OT}{TC/OC} \times 100$$

OC=Zero day control group value

OT=Zero day treated group value

TC=Test day control group value

TT=Test day treated group value

2. LDL and VLDL cholesterol levels were calculated according to the formula $LDL$ cholesterol in mg/dl =

$$\text{Total cholesterol} - HDL \text{ cholesterol} - \frac{\text{Triglyceride}}{5}$$

VLDL cholesterol in mg/dl=Total cholesterol−HDL cholesterol−LDL cholesterol

The invention claimed is:
1. A compound of formula (IIIe)

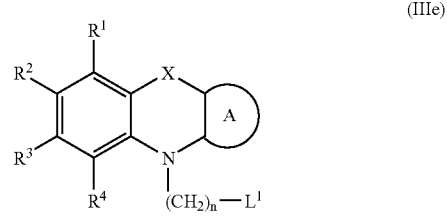

its tautomeric forms, its stereoisomers, or, its pharmaceutically acceptable salts, wherein $R^1$, $R^2$, $R^3$, and $R^4$ are the same or different and represent hydrogen, halogen, hydroxy, cyano, nitro, formyl, or optionally substituted groups selected from alkyl, cyclo($C_3$–$C_6$)alkyl alkoxy, cycloalkoxy, aryl, aryloxy, aralkyl, aralkoxy, heterocyclyl selected from the group consisting of aziridinyl, pyrrolidinyl, morpholinyl, piperidinyl and piperazinyl heteroaryl selected from the group consisting of pyridyl, thienyl, furyl, pyrrolyl, oxazolyl, thiazolyl, imidazolyl, oxadiazolyl, tetrazolyl, benzopyranyl and benzofuranyl; heteroaralkyl, heteroaryloxy, heteroaralkoxy, acyl, acyloxy, hydroxyalkyl, amino, acylamino, arylamino, aralkylamino, aminoalkyl, alkoxycarbonyl, aryloxycarbonyl, aralkyloxycarbonyl, alkylamino, alkoxyalkyl, aryloxyalkyl, aralkoxyalkyl, alkylthio, thioalkyl, aralkoxycarbonylamino, alkoxycarbonyl-amino, aryloxycarbonylamino, COOH, CONH$_2$, CONHMe, CONMe$_2$, CONHEt, CONHPh, SO$_2$OH, SO$_2$NH$_2$, SO$_2$NHMe, SO$_2$NMe$_2$, or SO$_2$NHCF$_3$; wherein when R$^1$, R$^2$, R$^3$ or R$^4$ is substituted, the substituent is selected from halogen, hydroxy, nitro, alkyl, cyclo(C$_3$–C$_6$)alkyl, alkoxy, cycloalkoxy, aryl, aralkyl, aralkoxyalkyl, heterocyclyl selected from the group consisting of aziridinyl, pyrrolidinyl, morpholinyl, piperidinyl and piperazinyl; heteroaryl selected from the group consisting of pyridyl, thienyl, furyl, pyrrolyl, oxazolyl, thiazolyl, imidazolyl, oxadiazolyl, tetrazolyl, benzopyranyl and benzofuranyl; heteroaralkyl, acyl, acyloxy, hydroxyalkyl, amino, acylamino, arylamino, aminoalkyl, aryloxy, alkoxycarbonyl, alkylamino, alkoxyalky, alkylthio, thioalkyl groups, COOH, CONH$_2$, CONHMe, CONMe$_2$, CONHEt, or CONHPh, or SO$_2$OH, or SO$_2$NH$_2$, SO$_2$NHMe, SO$_2$NMe$_2$, or SO$_2$NHCF$_3$; A is an optionally substituted benzene ring wherein when A is substituted, the substituent is selected from halogen, hydroxy, nitro, alkyl, cyclo(C$_3$–C$_6$)alkyl, alkoxy, cycloalkoxy, aryl, aralkyl, aralkoxyalkyl, heterocyclyl selected from the group consisting of aziridinyl, pyrrolidinyl, morpholinyl, piperidinyl and piperazinyl; heteroaryl selected from the group consisting of pyridyl, thienyl, furyl, pyrrolyl, oxazolyl, thiazolyl, imidazolyl, oxadiazolyl, tetrazolyl, benzopyranyl and benzofuranyl; heteroaralkyl, acyl, acyloxy, hydroxyalkyl, amino, acylamino, arylamino, aminoalkyl, aryloxy, alkoxycarbonyl, alkylamino, alkoxyalky, alkylthio, thioalkyl groups, COOH, CONH$_2$, CONHMe, CONMe$_2$, CONHEt, CONHPh, SO$_2$OH, SO$_2$NH$_2$, SO$_2$NHMe, SO$_2$NMe$_2$, or SO$_2$NHCF$_3$; X represents oxygen, n is an integer of 1 or 2 and L$^1$ is methane sulphonate, or trifluoromethane sulphonate.

\* \* \* \* \*